United States Patent
Molina et al.

(10) Patent No.: US 12,318,617 B2
(45) Date of Patent: Jun. 3, 2025

(54) ELECTRICAL STIMULATION THERAPY

(71) Applicant: Medtronic, Inc., Minneapolis, MN (US)

(72) Inventors: Rene A. Molina, Maple Grove, MN (US); Robert S. Raike, Minneapolis, MN (US); Benjamin P. Isaacson, Mahtomedi, MN (US); Christopher L. Pulliam, Plymouth, MN (US); Abbey Beuning Holt Becker, Shoreview, MN (US); Michelle A. Case, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 396 days.

(21) Appl. No.: 17/651,888

(22) Filed: Feb. 21, 2022

(65) Prior Publication Data

US 2022/0266032 A1    Aug. 25, 2022

Related U.S. Application Data

(60) Provisional application No. 63/152,984, filed on Feb. 24, 2021.

(51) Int. Cl.
| | |
|---|---|
| *A61N 1/36* | (2006.01) |
| *A61N 1/02* | (2006.01) |
| *A61N 1/05* | (2006.01) |
| *A61N 1/372* | (2006.01) |

(52) U.S. Cl.
CPC ......... *A61N 1/36178* (2013.01); *A61N 1/025* (2013.01); *A61N 1/0534* (2013.01); *A61N 1/36185* (2013.01); *A61N 1/37235* (2013.01)

(58) Field of Classification Search
CPC .. A61N 1/36178; A61N 1/025; A61N 1/0534; A61N 1/36185; A61N 1/37235
See application file for complete search history.

(56) References Cited

U.S. PATENT DOCUMENTS

| | | | |
|---|---|---|---|
| 8,340,775 B1 * | 12/2012 | Cullen | A61N 1/37247 607/46 |
| 8,473,059 B2 * | 6/2013 | Tass | A61N 1/36082 607/45 |
| 8,532,757 B2 * | 9/2013 | Molnar | A61N 1/36185 607/45 |
| 8,538,513 B2 * | 9/2013 | Molnar | A61N 1/36185 607/45 |
| 10,617,869 B2 * | 4/2020 | Tass | A61N 1/36139 |

(Continued)

*Primary Examiner* — Eric D. Bertram
(74) *Attorney, Agent, or Firm* — Shumaker & Sieffert, P.A.

(57) ABSTRACT

A medical device for providing electrical stimulation to a brain of a patient includes one or more processors. The one or more processors are configured to determine a first set of parameters of a first electrical signal that is delivered via a first electrode configured to apply electrical stimulation to a first region of the brain and to determine a second set of parameters of a second electrical signal based on the first set of parameters. The second electrical signal is delivered via a second electrode configured to apply electrical stimulation to a second region of the brain. The one or more processors are further configured to deliver, with the first electrode, the first electrical signal having the first set of parameters and to deliver, with the second electrode, the second electrical signal having the second set of parameters.

17 Claims, 18 Drawing Sheets

(56) References Cited

U.S. PATENT DOCUMENTS

| | | | | |
|---|---|---|---|---|
| 11,596,791 | B2* | 3/2023 | Wong | A61N 1/36014 |
| 2012/0071947 | A1* | 3/2012 | Gupta | A61N 1/36139 |
| | | | | 607/45 |
| 2014/0058189 | A1* | 2/2014 | Stubbeman | A61M 21/02 |
| | | | | 600/13 |
| 2017/0157398 | A1* | 6/2017 | Wong | A61N 1/36031 |
| 2017/0361103 | A1* | 12/2017 | Hadjiyski | A61N 1/0551 |
| 2019/0175040 | A1* | 6/2019 | Arcot Desai | A61B 5/6868 |
| 2021/0001126 | A1* | 1/2021 | Wu | A61N 1/0534 |
| 2021/0187297 | A1* | 6/2021 | Pulliam | A61B 5/383 |
| 2021/0275817 | A1* | 9/2021 | Li | A61N 1/3615 |
| 2022/0032063 | A1* | 2/2022 | Molina | A61N 1/36171 |
| 2022/0040485 | A1* | 2/2022 | Li | A61B 5/6877 |
| 2022/0176134 | A1* | 6/2022 | Chouinard | A61N 1/36082 |

* cited by examiner

ELECTRICAL STIMULATION THERAPY

This application claims the benefit of U.S. Provisional Patent Application No. 63/152,984, filed 24 Feb. 2021, the entire contents of which is incorporated herein by reference.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patent. For bipolar stimulation, the electrodes used for stimulation may be on one or more leads. For unipolar stimulation, the electrodes may be on one or more leads, and an electrode on a stimulator housing located remotely from the target site (e.g., near clavicle). It may be possible to use leadless stimulation using electrodes mounted on the stimulation housing. Hence, electrical stimulation is used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as stimulation parameters. A set of parameters, such as a set including electrode combination, electrode polarity, amplitude, pulse width, and pulse rate, may be referred to as a program in the sense that they define the electrical stimulation therapy to be delivered to the patient.

SUMMARY

This disclosure describes example techniques for electrical stimulation therapy to desynchronize (e.g., reduce overly synchronized nodes) regions of a brain of a patient. In example techniques, a medical device (e.g., implantable medical device (IMD) or programmer) may be configured to deliver a first burst of pulses to a first region of the brain and deliver a second burst of pulses to a second region of the brain after delivering the first burst of pulses to the first region of the brain. In some examples, the medical device may be configured to deliver a first portion of interleaved pulses to a first region of the brain and deliver a second portion of the interleaved pulses to the second region of the brain. A medical device may be configured to deliver a first portion of concurrent pulses to a first region of the brain and deliver a second portion of the concurrent pulses to the second region of the brain. Delivering bursts of pulses, interleaved pulses, and/or concurrent pulses to regions of the brain of a patient (e.g., a first hemisphere and a second hemisphere or different portions of one hemisphere) may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders.

In one example, this disclosure describes a medical device for providing electrical stimulation to a brain of a patient. The medical device includes one or more processors configured to determine a first set of parameters of a first electrical signal that is delivered via a first electrode configured to apply electrical stimulation to a first region of the brain and to determine a second set of parameters of a second electrical signal based on the first set of parameters. The second electrical signal is delivered via a second electrode configured to apply electrical stimulation to a second region of the brain. The one or more processors are further configured to deliver, with the first electrode, the first electrical signal having the first set of parameters and to deliver, with the second electrode, the second electrical signal having the second set of parameters.

In another example, this disclosure describes a method for providing electrical stimulation to a brain of a patient includes determining, with one or more processors, a first set of parameters of a first electrical signal that is delivered via a first electrode configured to apply electrical stimulation to a first region of the brain and determining, with the one or more processors, a second set of parameters of a second electrical signal based on the first set of parameters, wherein the second electrical signal is delivered via a second electrode configured to apply electrical stimulation to a second region of the brain. The method further includes delivering, with the one or more processors and with the first electrode, the first electrical signal having the first set of parameters and delivering, with the one or more processors and with the second electrode, the second electrical signal having the second set of parameters.

In one example, this disclosure describes a medical device for providing electrical stimulation to a brain of a patient. The medical device includes a first electrode, a second electrode, and one or more processors configured to determine a first set of parameters of a first electrical signal that is delivered via the first electrode configured to apply electrical stimulation to a first region of the brain and to determine a second set of parameters of a second electrical signal based on the first set of parameters. The second electrical signal is delivered via the second electrode configured to apply electrical stimulation to a second region of the brain. The one or more processors are further configured to deliver, with the first electrode, the first electrical signal having the first set of parameters and to deliver, with the second electrode, the second electrical signal having the second set of parameters.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
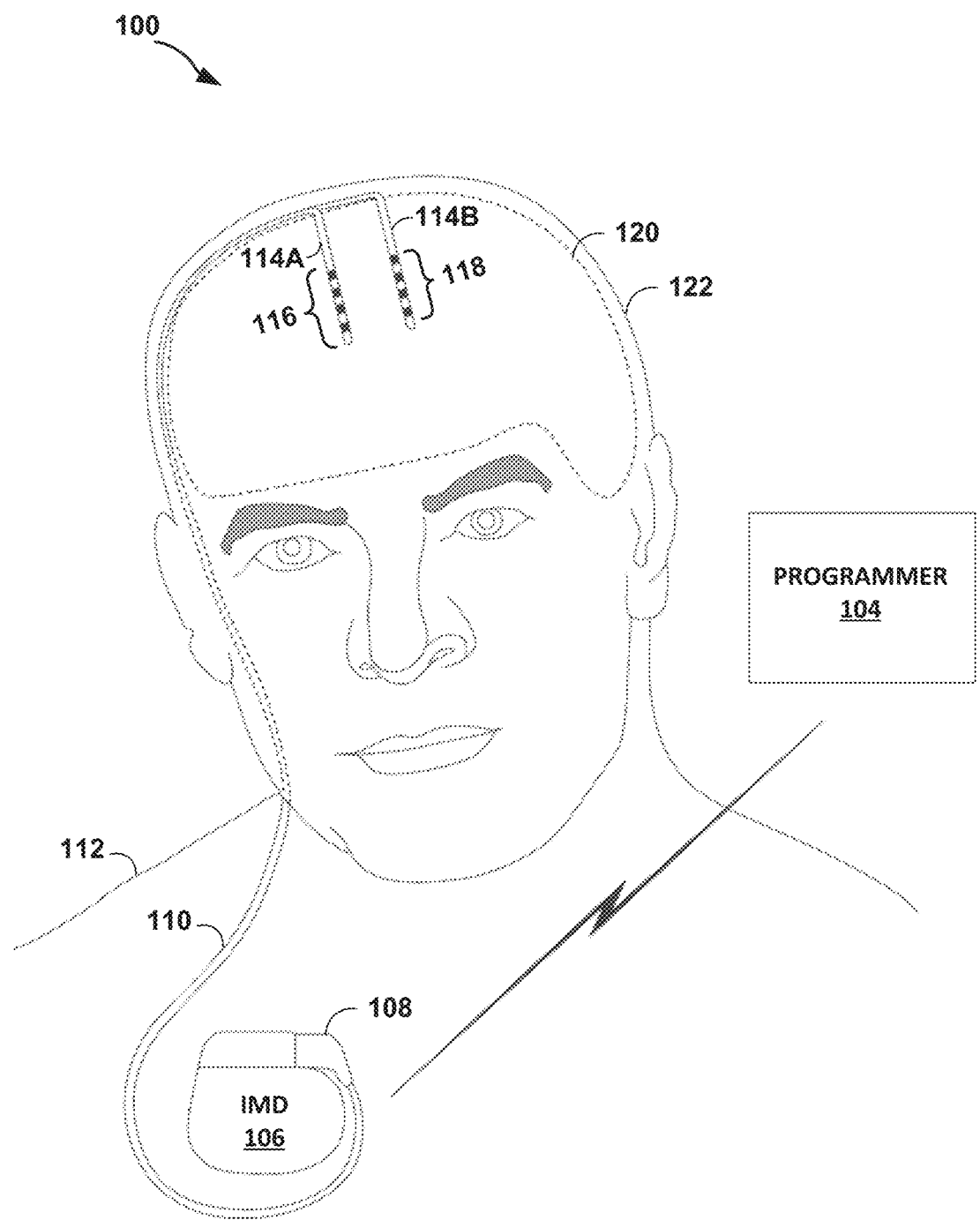
FIG. 1 is a conceptual diagram illustrating an example system that includes an implantable medical device (IMD) configured to deliver electrical stimulation to a patient according to an example of the techniques of the disclosure.

This disclosure describes example techniques for multi-nodal desynchronization, in modulation (e.g., neuromodulation). For example, techniques described herein may be directed to implantation and actuation of delivering stimulation intended to desynchronize multiple nodes in a network of a brain. Nodes (e.g., regions of a brain of a patient) may be either coordinated (e.g., coherent) or desynchronized across hemispheres of the brain. Such coupling of nodes of the brain may be associated with Parkinson's diseases, neurorehabilitation and/or unilateral motor program, and/or lateralized regions of specialization (e.g., unilateral motor task activates bilateral subcortical motor network). For example, low-beta cortico-pallidal coherence may decrease during movement and may correlate with overall reaction time. Somatotopic homunculi may be represented in the subthalamic nucleus. Task specific inter-hemispheric may be coupled in a human subthalamic nuclei. Exaggerated phase—amplitude may be coupling in the primary motor cortex in Parkinson disease.

Techniques described herein may help to desynchronize the coupling of nodes of the brain using patterns (e.g., bursts of pulses, interleaved pulses, or concurrent pulses) to modulate a coupling of nodes in the brain. Synchronization of nodes of the brain may refer to an increase in oscillatory activity between neurons, while desynchronization of nodes of the brain may refer a decrease in the oscillatory activity between neurons. Techniques described herein may use sensing (e.g., correlations and/or coherence between nodes, other coupling metrics) to inform the patterns to help to desynchronize the brain. For example, a medical device (e.g., implantable medical device (IMD) or programmer) may be configured to deliver electrical stimulation for multi-nodal desynchronization using one or more of burst interleaved (e.g., bursts of pulses), pulsatile interleaved (e.g., interleaved pulses), or simultaneous (e.g., concurrent pulses) patterns. Each pattern (e.g., bursts of pulses, interleaved pulses, or concurrent pulses) may include symmetric versions. For instance, the medical device may be configured to apply a first burst of pulses and a second burst of pulses where the first and second burst of pulses comprise a same number of pulses and/or where the first and second burst of pulses comprise different numbers of pulses. Moreover, techniques described herein may apply to two or more nodes. For example, the medical device may apply a first burst of pulses to a first node of the brain, a second burst of pulses to a second node of the brain, and a third burst of pulses to a third node of the brain.

Based on the above techniques, the medical device may help to desynchronize the coupling of nodes of the brain, which may improve a therapy provided to the patient. For example, desynchronizing the coupling of nodes of the brain may help to mitigate one or more symptoms associated with Parkinson's diseases, neurorehabilitation and/or unilateral motor program, and/or lateralized regions of specialization (e.g., unilateral motor task activates bilateral subcortical motor network). In this way, the medical device may be configured to apply electrical stimulation with one or more patterns to help to improve a therapy provided to a patient.

FIG. 1 is a conceptual diagram illustrating an example system 100 that includes an implantable medical device (IMD) 106 configured to deliver adaptive deep brain stimulation (DBS) to a patient 112. DBS may be adaptive in the sense that IMD 106 may adjust, increase, or decrease the magnitude of one or more parameters of the DBS in response to changes in patient activity or movement, a severity of one or more symptoms of a disease of the patient, a presence of one or more side effects due to the DBS, or one or more sensed signals of the patient.

For instance, one example of system 100 is a bi-directional DBS system with capabilities to both deliver stimulation and sense intrinsic neuronal signals. System 100 may provide for "closed-loop" therapy where IMD 106 may continuously monitor the state of certain biomarker signals and deliver stimulation according to pre-programmed routines based on the biomarker signals.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120. In some examples, unipolar stimulation may be possible where one electrode is on the housing of IMD 106.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. Examples of neurological brain signals include, but are not limited to, bioelectric signals generated from local field potentials (LFP) sensed within one or more regions of brain 120. Electroencephalogram (EEG) signal or an electrocorticogram (ECoG) signal are also examples of bioelectric signals. For example, neurons generate the bioelectric signals, and if measured at depth, it is LFP, if measured on the coretex, it is ECoG, and if on scalp, it is EEG. In this disclosure, the term "oscillatory signal source" is used to describe a signal source that generates bioelectric signals.

One example of the feature of interest (e.g., biomarker) within the LFPs is synchronized beta frequency band (13-33 Hz) LFP activity recorded within the sensorimotor region of the subthalamic nucleus (STN) in Parkinson's disease patients. The source of the LFP activity can be considered as an oscillatory signal source, within the brain of the patient, that outputs an oscillatory electrical voltage signal that is sensed by one or more of electrodes 116 and/or 118. The suppression of pathological beta activity (e.g., suppression or squelching of the signal component of the bioelectric signals generated from the oscillatory LFP signal source that is within the beta frequency band) by both medication and DBS may correlate with improvements in the motor symptoms of patients who have Parkinson's disease.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both stimulation electrode combinations and sense electrode combinations may be selected from the same set of electrodes 116, 118. In other examples, the electrodes used for delivering electrical stimulation may be different than the electrodes used for sensing neurological brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a selected therapy program. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. As described further, the electrical stimulation generated by IMD 106 may generate, for example, burst pulses, interleaved pulses, or concurrent pulses.

In some examples, electrodes 116, 118 may be radially-segmented DBS arrays (rDBSA) of electrodes. Radially-segmented DBS arrays refer to electrodes that are segmented radially along the lead. As one example, leads 114A and 114B may include a first set of electrodes arranged circumferentially around leads 114A and 114B that are all at the same height level on leads 114A and 114B. Each of the electrodes in the first set of electrodes is a separate segmented electrode and form a level of radially-segmented array of electrodes. Leads 114A and 114B may include a second set of electrodes arranged circumferentially around leads 114A and 114B that are all at the same height level on leads 114A and 114B. Each of the electrodes in the first set of electrodes is a separate segmented electrode and form a level of radially-segmented array of electrodes. The rDBSA electrodes may be beneficial for directional stimulation and sensing.

The signal component in the beta frequency band is described as one example, and the techniques are applicable to other types of LFP activity. Furthermore, the example techniques are not limited to examples where electrodes 116, 118 are an rDBSA of electrodes. The example of using rDBSA of electrodes is described as a way of directional stimulation and sensing. However, the example techniques are also useable in examples where directional stimulation and sensing are not available or are not used. Moreover, there may be other ways of performing directional stimulation and sensing that do not require the use of an rDBSA of electrodes.

To suppress the signal component having the beta frequency band from the oscillatory signal source, IMD 106 may output an electrical stimulation signal that alters the way in which neurons of the oscillatory signal source produce signals. For example, the electrical stimulation either directly inhibits a certain neuronal population that includes the oscillatory signal source or excites one group of neurons which in turn suppresses another group of neurons (e.g., network effect). The stimulation may act on the neurons directly, and not necessarily on the signals the neurons (e.g., oscillatory signal source) produces.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres (or in just one hemisphere in some examples), respectively, of patient 112 in order to deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. For example, the target tissue site may be the location of the oscillatory signal source that generates the bioelectric signal having a signal component in the beta frequency band. The stimulation electrodes used to deliver stimulation to the target tissue site may be those that are most proximal to the oscillatory signal source, e.g., using the example techniques described in this disclosure. Other lead 114 and IMD 106 implant sites are contemplated. For example, IMD 106 may be implanted on or within cranium 122, in some examples. Leads 114A and 114B may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue.

In some examples, a housing of IMD 106 may include one or more stimulation and/or sensing electrodes. In some examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the parameters of the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106.

Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

However, in some examples, IMD 106 or programmer 104 (e.g., a medical device), alone or in combination, may automatically determine electrode configuration and therapy parameters. For example, the medical device may determine which electrodes to use for stimulation based on which electrodes are most proximal to the oscillatory signal source. In some examples, programmer 104 may output information indicating the selected electrode configuration for stimulation and the determined stimulation amplitude or other therapy parameter for the clinician or physician to review and confirm before IMD 106 delivers therapy via the selected electrode configuration with the determined stimulation amplitude.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112. Further, an IMD may provide other electrical stimulation such as spinal cord stimulation to treat a movement disorder.

According to the techniques of the disclosure, a medical device (e.g., IMD 106 or programmer 104 either alone or in combination) of system 100 may be configured to deliver a first electrical signal at electrode 116 to a first region of a brain and deliver a second electrical signal at electrode 118 to a second region of a brain based on the first electrical signal. For example, one or more processors of system 100 may determine a first set of parameters for the first electrical signal and determine a second set of parameters for the second electrical signal based on the first set of parameters.

For example, to determine the first set of parameters, the one or more processors may determine a first plurality of pulses that form a first burst of pulses. In this example, to determine the second set parameters, the one or more processors may set a second plurality of pulses that form a second burst of pulses to occur after delivering the first burst of pulses. For example, the one or more processors may determine a delay between delivering the first burst of pulses and starting to deliver the second burst of pulses based on a temporal or spatial proximity of the first region of the brain and the second region of the brain or the "strength" of the synchrony between the first region of the brain and the second region of the brain.

In this way, the first electrical signal may provide the first burst of pulses in a first region of a brain of patient 112 that is coordinated with the second electrical signal providing the second burst of pulses in a second region of a brain of patient 112, which may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders.

For example, to determine the first set of parameters, the one or more processors may determine a first portion of a plurality of interleaved pulses. In this example, to determine the second set parameters, the one or more processors may determine a second portion of the plurality of interleaved pulses. For instance, the first portion of the plurality of interleaved pulses may comprise a first pulse and a third pulse and the second portion of the plurality of interleaved pulses may comprise a second pulse and a fourth pulse. In this instance, the one or more processors may set the second pulse to occur after the first pulse and before the third pulse and setting the fourth pulse to occur after the third pulse. In this way, the first electrical signal may provide the first portion of the plurality of interleaved pulses in a first region of a brain of patient 112 that is coordinated with the second electrical signal providing the second portion of the plurality of interleaved pulses in a second region of a brain of patient 112, which may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders.

To determine the first set of parameters, the one or more processors may determine a first portion of a plurality of concurrent pulses. In this example, to determine the second set parameters, the one or more processors may determine a second portion of the concurrent of interleaved pulses to be delivered concurrently with the delivery of the first portion of the plurality of concurrent pulses. In this way, the first electrical signal may provide the first portion of the plurality of concurrent pulses in a first region of a brain of patient 112 that is coordinated with the second electrical signal providing the second portion of the plurality of concurrent pulses in a second region of a brain of patient 112, which may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders.

Figure 2:
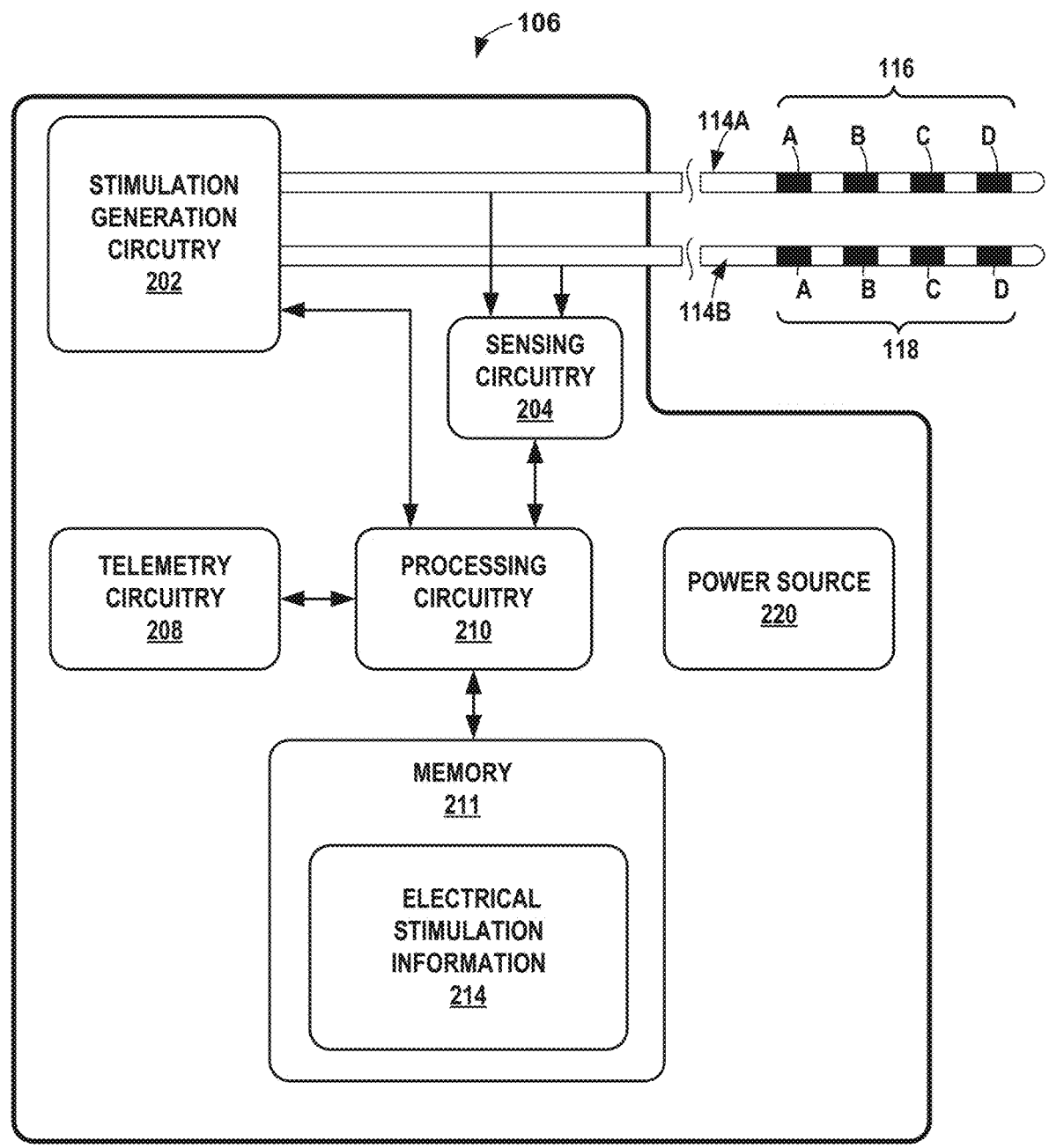
FIG. 2 is a block diagram of the example IMD of FIG. 1 for delivering electrical stimulation according to an example of the techniques of the disclosure.

FIG. 2 is a block diagram of the example IMD 106 of FIG. 1 for delivering adaptive deep brain stimulation therapy. In the example shown in FIG. 2, IMD 106 includes processing circuitry 210, memory 211, stimulation generation circuitry 202, sensing circuitry 204, telemetry circuitry 208, and power source 220. Each of these circuits may be or include electrical circuitry configured to perform the functions attributed to each respective circuit. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 106 to perform various functions. Memory 211 may be a storage device or other non-transitory medium.

In the example shown in FIG. 2, memory 211 stores electrical stimulation information 214. Electrical stimulation information 214 may include program parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Stimulation generation circuitry 202, under the control of processing circuitry 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 90 to 170 Hertz or such as approximately 90 Hertz.
2. In the case of a voltage controlled system, Voltage Amplitude: between approximately 0.1 volts and approximately 50 volts, such as between approximately 2 volts and approximately 3 volts.
3. In the case of a current controlled system, Current Amplitude: between approximately 1 milliamps to approximately 3.5 milliamps, such as between approximately 1.0 milliamps and approximately 1.75 milliamps.
4. Pulse Width: between approximately 50 microseconds and approximately 500 microseconds, such as between approximately 50 microseconds and approximately 200 microseconds.

Accordingly, in some examples, stimulation generation circuitry 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generation circuitry 202 according to therapy programs 214 stored in memory 211 to apply particular stimulation parameter values specified by one or more of programs, such as voltage amplitude or current amplitude, pulse width, and/or pulse rate.

In the example shown in FIG. 2, the set of electrodes 116 includes electrodes 116A, 116B, 116C, and 116D, and the set of electrodes 118 includes electrodes 118A, 118B, 118C, and 118D. In the example of FIG. 2, IMD 106 does not include switch circuitry. In some examples, however, processing circuitry 210 may control switch circuitry to apply the stimulation signals generated by stimulation generation circuitry 202 to selected combinations of electrodes 116, 118. In particular, the switch circuitry may couple stimulation signals to selected conductors within leads 114, which, in turn, deliver the stimulation signals across selected electrodes 116, 118. The switch circuitry may be a switch array, switch matrix, multiplexer, or any other type of switching module configured to selectively couple stimulation energy to selected electrodes 116, 118 and to selectively sense neurological brain signals with selected electrodes 116, 118.

Hence, stimulation generation circuitry 202 may be coupled to electrodes 116, 118 via the switch circuitry and conductors within leads 114.

Stimulation generation circuitry 202 may be a single channel or multi-channel stimulation generator. In particular, stimulation generation circuitry 202 may be capable of delivering a single stimulation pulse, multiple stimulation pulses, or a continuous signal at a given time via a single electrode combination or multiple stimulation pulses at a given time via multiple electrode combinations. In some examples, however, stimulation generation circuitry 202 may be configured to deliver multiple channels on a time-interleaved basis. For example, stimulation generation circuitry 202 may comprise multiple voltage or current sources and sinks that are coupled to respective electrodes to drive the electrodes as cathodes or anodes.

Electrodes 116, 118 on respective leads 114 may be constructed of a variety of different designs. For example, one or both of leads 114 may include two or more electrodes at each longitudinal location along the length of the lead, such as multiple electrodes, e.g., arranged as segments, at different perimeter locations around the perimeter of the lead at each of the locations A, B, C, and D.

As an example, one or both of leads 114 may include radially-segmented DBS arrays (rDBSA) of electrodes. In the rDBSA, as one example, there may be a first ring electrode of electrodes 116 around the perimeter of lead 114A at a first longitudinal location on lead 114A (e.g., location A). Below the first ring electrode, there may be three segmented electrodes of electrodes 116 around the perimeter of lead 114A at a second longitudinal location on lead 114A (e.g., location B). Below the three segmented electrodes, there may be another set of three segmented electrodes of electrodes 116 around the perimeter of lead 114A at a third longitudinal location of lead 114A (e.g., location C). Below the three segmented electrodes, there may be a second ring electrode of electrodes 116 around the perimeter of lead 114A (e.g., location D). Electrodes 118 may be similarly positioned along lead 114B. An example of rDBSA arrays of electrodes on a lead is described in more detail with respect to FIG. 4.

The above is one example of the rDBSA array of electrodes, and the example techniques should not be considered limited to such an example. There may be other configurations of electrodes for DBS. Moreover, the example techniques are not limited to DBS, and other electrode configurations are possible.

In one example, the electrodes 116, 118 may be electrically coupled to stimulation generation circuitry 202 via respective wires that are straight or coiled within the housing of the lead and run to a connector at the proximal end of the lead. In another example, each of the electrodes 116, 118 of the leads 114 may be electrodes deposited on a thin film. The thin film may include an electrically conductive trace for each electrode that runs the length of the thin film to a proximal end connector. The thin film may then be wrapped (e.g., a helical wrap) around an internal member to form the leads 114. These and other constructions may be used to create a lead with a complex electrode geometry.

Although sensing circuitry 204 is incorporated into a common housing with stimulation generation circuitry 202 and processing circuitry 210 in FIG. 2, in other examples, sensing circuitry 204 may be in a separate housing from IMD 106 and may communicate with processing circuitry 210 via wired or wireless communication techniques. Example neurological brain signals include, but are not limited to, a signal generated from local field potentials (LFPs) within one or more regions of brain 120. EEG and ECoG signals are examples of local field potentials that may be measured within brain 120. LFPs, EEG and ECoG may be different measurements of the same bioelectric signals in the brain. The neurons generate the signals, and if measured at depth, it is LFP, if measured on the coretex, it is ECoG, if on the scalp, it is EEG. In general, the bioelectric signals may be formed by one or more oscillatory signal sources. The set of electrodes 116 and 118 that are most proximate to the oscillatory signal sources are good candidates to use for delivering therapy.

Telemetry circuitry 208 supports wireless communication between IMD 106 and an external programmer 104 or another computing device under the control of processing circuitry 210. Processing circuitry 210 of IMD 106 may receive, as updates to programs, values for various stimulation parameters such as magnitude and electrode combination, from programmer 104 via telemetry circuitry 208. The updates to the therapy programs may be stored within therapy programs 214 portion of memory 211. Telemetry circuitry 208 in IMD 106, as well as telemetry modules in other devices and systems described herein, such as programmer 104, may accomplish communication by radiofrequency (RF) communication techniques. In addition, telemetry circuitry 208 may communicate with external medical device programmer 104 via proximal inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 104. In some examples, power requirements may be small enough to allow IMD 104 to utilize patient motion and implement a kinetic energy-scavenging device to trickle charge a rechargeable battery. In other examples, traditional batteries may be used for a limited period of time.

In one example, processing circuitry 210 of IMD 106 senses, via electrodes 116, 118 interposed along leads 114 (and sensing circuitry 204), one or more bioelectric signals of brain 120 of patient 112. Further, processing circuitry 210 of IMD 106 delivers, via electrodes 116, 118 (and stimulation generation circuitry 202), electrical stimulation therapy to patient 112 based on the sensed one or more bioelectric signals of brain 120. The adaptive DBS therapy is defined by electrical stimulation information 214. For example, electrical stimulation information 214 may include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. Processing circuitry 210, via electrodes 116, 118, delivers to patient 112 adaptive DBS and may adjust one or more parameters defining the electrical stimulation based on corresponding parameters of the sensed one or more bioelectric signals of brain 120.

In some examples, processing circuitry 210 may continuously measure the one or more bioelectric signals in real time. In other examples, processing circuitry 210 may periodically sample the one or more bioelectric signals according to a predetermined frequency or after a predetermined amount of time. In some examples, processing circuitry 210 may periodically sample the signal at a frequency of approximately 150 Hertz.

According to the techniques of the disclosure, processing circuitry 210 may be configured to deliver a first electrical signal at electrode 116 and deliver a second electrical signal at electrode 118. For example, processing circuitry 210 may be configured to deliver a first burst of pulses to a first region of the brain and deliver a second burst of pulses to a second region of the brain after applying the first burst of pulses to the first region of the brain. For instance, processing circuitry 210 may generate the first electrical signal to comprise a first plurality of pulses that form a first burst of pulses. In this example, processing circuitry 210 may generate the second electrical signal to comprise a second plurality of pulses that form a second burst of pulses after generating the first burst of pulses.

One or more parameters of first burst of pulses and/or the second burst of pulses may be specified by electrical stimulation information 214. For instance, electrical stimulation information 214 may specify that pulses of the first burst of pulses comprise a continuous-time signal (e.g., a cosine wave or a sine wave), set at, for example, 130 Hz. In some instances, electrical stimulation information 214 may specify that the first burst of pulses is to be output at a first electrode (e.g., electrode 116A) associated with a first region (e.g., a first portion of a first hemisphere of a brain of the patient) and may specify that the second burst of pulses is to be output at a second electrode (e.g., electrode 118A) associated with a second region (e.g., a second portion of the first hemisphere or a second hemisphere of a brain of the patient).

The first burst of pulses may correspond to the second burst of pulses. For example, the first burst of pulses may comprise a first number of pulses equal to a second number of pulses of the second burst of pulses. In some examples, the first burst of pulses comprises a first duration that corresponds to (e.g., equals) a second duration of the second burst of pulses. In some examples, the first burst of pulses may not correspond to the second burst of pulses. For example, the first burst of pulses may comprise a first number of pulses that is different than (e.g., does not equal to) a second number of pulses of the second burst of pulses. In some examples, the first burst of pulses comprises a first duration that is different than a second duration of the second burst of pulses.

In some examples, processing circuitry 210 may be configured to deliver a first portion of interleaved pulses to a first region of the brain and deliver a second portion of the interleaved pulses to the second region of the brain. For example, processing circuitry 210 may generate the first portion of the plurality of interleaved pulses to comprise a first pulse and a third pulse. In this example, processing circuitry 210 may generate the second portion of the plurality of interleaved pulses to comprise a second pulse after the first pulse and before the third pulse and generate a fourth pulse after the third pulse.

One or more parameters of first and/or the second portion of the plurality of interleaved pulses may be specified by electrical stimulation information 214. For instance, electrical stimulation information 214 may specify that pulses of the first portion of a plurality of interleaved pulses comprise a continuous-time signal (e.g., a cosine wave or a sine wave), set at, for example, 130 Hz. In some instances, electrical stimulation information 214 may specify that the first portion of a plurality of interleaved pulses is to be output at a first electrode (e.g., electrode 116A) associated with a first region (e.g., a first portion of a first hemisphere of a brain of the patient) and may specify that the second portion of a plurality of interleaved pulses is to be output at a second electrode (e.g., electrode 118A) associated with a second region (e.g., a second portion of the first hemisphere or a second hemisphere of a brain of the patient).

The first portion of a plurality of interleaved pulses may correspond to the second portion of a plurality of interleaved pulses. For example, the first portion of a plurality of interleaved pulses may comprise a first number of pulses equal to a second number of pulses of the second portion of a plurality of interleaved pulses. In some examples, the first portion of a plurality of interleaved pulses may not correspond to the second portion of a plurality of interleaved pulses. For example, the first portion of a plurality of interleaved pulses may comprise a first number of pulses that is different than a second number of pulses of the second portion of a plurality of interleaved pulses.

Processing circuitry 210 may be configured to deliver a first portion of concurrent pulses to a first region of the brain and deliver a second portion of the concurrent pulses to the second region of the brain. For example, processing circuitry 210 may generate the first portion of the plurality of concurrent pulses to comprise a first pulse and a third pulse. In this example, processing circuitry 210 may generate the second portion of the plurality of concurrent pulses to comprise a second pulse concurrently with the first pulse (e.g., simultaneously or substantially simultaneously) and generate a fourth pulse concurrently with the third pulse.

One or more parameters of first and/or the second portion of the plurality of concurrent pulses may be specified by electrical stimulation information 214. For instance, electrical stimulation information 214 may specify that pulses of the first portion of a plurality of concurrent pulses comprise a continuous-time signal (e.g., a cosine wave or a sine wave), set at, for example, 130 Hz. In some instances, electrical stimulation information 214 may specify that the first portion of a plurality of concurrent pulses is to be output at a first electrode (e.g., electrode 116A) associated with a first region (e.g., a first portion of a first hemisphere of a brain of the patient) and may specify that the second portion of a plurality of concurrent pulses is to be output at a second electrode (e.g., electrode 118A) associated with a second region (e.g., a second portion of the first hemisphere or a second hemisphere of a brain of the patient).

In accordance with the techniques of the disclosure, configuring processing circuitry 210 to deliver a first electrical signal and deliver a second electrical signal based on the first electrical signal (e.g., using bursts of pulses, interleaved pulses, and/or concurrent pulses) to regions of the brain of a patient may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders. In this way, processing circuitry 210 may help to desynchronize regions of a brain of a patient, which may improve a therapy provided to the patient.

For example, processing circuitry 210, with sensing circuitry 204, may determine whether neural data (e.g., beta signals) in a first region of the brain of a patient and a second region of the brain are overly synchronized (e.g., oscillatory activity between neurons exceeds a threshold). In response to determining that the first region of the brain of the patient and the second region of the brain are overly synchronized, processing circuitry 210 may deliver a first electrical signal at the first region of the brain and deliver the second electrical signal at the second region of the brain to desynchronize (e.g., reduce neural data (e.g., beta signals) in the first region and the second region). For instance, processing circuitry 210, with stimulation generation circuitry 202, may provide a first burst of pulses in the first region that is coordinated with the second electrical signal providing the second burst of pulses in the second region. In some instances, processing circuitry 210, with stimulation generation circuitry 202, may provide a first portion of the plurality of interleaved pulses in the first region that is coordinated with the second electrical signal providing a second portion of the plurality of interleaved pulses in the second region. Processing circuitry 210, with stimulation generation circuitry 202, may provide a first portion of the plurality of concurrent pulses in the first region that is coordinated with the second electrical signal providing a second portion of the plurality of concurrent pulses in the second region.

Processing circuitry 210 may select between bursts of pulses, interleaved pulses, or concurrent pulses. For example, processing circuitry 210 may select a pulse type (e.g., bursts of pulses, interleaved pulses, or concurrent pulses) based on a user selection. In some examples, processing circuitry 210 may select the pulse type based on time scales. In some examples, processing circuitry 210 may restrict options (e.g., required to deliver concurrent not interleaved to get a desired pulse count within a certain duration).

Processing circuitry 210, with sensing circuitry 204, may periodically (e.g., hourly, daily, weekly, or monthly) determine whether the first region of the brain of a patient and a second region of the brain are overly synchronized. For example, processing circuitry 210 may sense patient parameters while refraining from delivering the first electrical signal and the second electrical signal. In this example, processing circuitry 210 may determine whether the first region of the brain of a patient and a second region of the brain are overly synchronized based on the patient parameters. Processing circuitry 210 may continue to deliver the first electrical signal and the second electrical signal when the first region of the brain of a patient and a second region of the brain are overly synchronized. However, processing circuitry 210 may stop delivering the first electrical signal and the second electrical signal when the first region of the brain of a patient and a second region of the brain are not overly synchronized.

Figure 3:
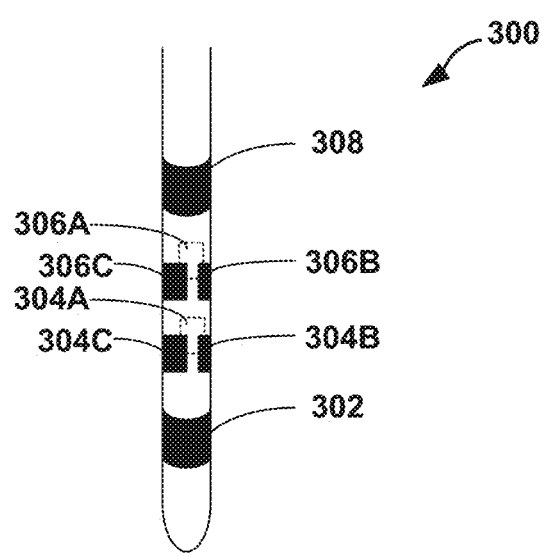
FIG. 3 is a conceptual diagram illustrating an example of a lead with segmented and ring electrodes.

FIG. 3 is a conceptual diagram illustrating an example of a lead 300 with segmented and ring electrodes. Lead 300 is an example of leads 114A and 114B. Processing circuitry 210 may be configured to output electrical signals using, for example, bursts of pulses, interleaved pulses, and/or concurrent pulses at one or more of ring electrode 302, segmented electrodes 304A-304C, segmented electrodes 306A-306C, or ring electrode 308.

The lead radius for lead 300 is approximate 0.66 mm. Lead 300 includes ring electrode 302, segmented electrodes 304A-304C, segmented electrodes 306A-306C, and ring electrode 308. The electrodes on lead 300 may be vertically (e.g., axially) spaced by a distance D (e.g., 2 mm to 3 mm). For example, assume that the z-coordinate for ring electrode 302 is 0. In this example, the z-coordinate for segment electrodes 304A-304C is D, the z-coordinate for segment electrodes 306A-306D is 2D, and the z-coordinate for ring electrode 308 is 3D.

Segmented electrodes 304A-304C may be all at the same vertical level (e.g., axial level), and segmented electrodes 306A-306C may be all at the same vertical level (e.g., axial level). In this example, the angular separation between segmented electrodes 304A-304C may be 120-degrees. Therefore, segmented electrodes 304A and 306A are on the backside of lead 300 and shown in dashed lines.

Figure 4:
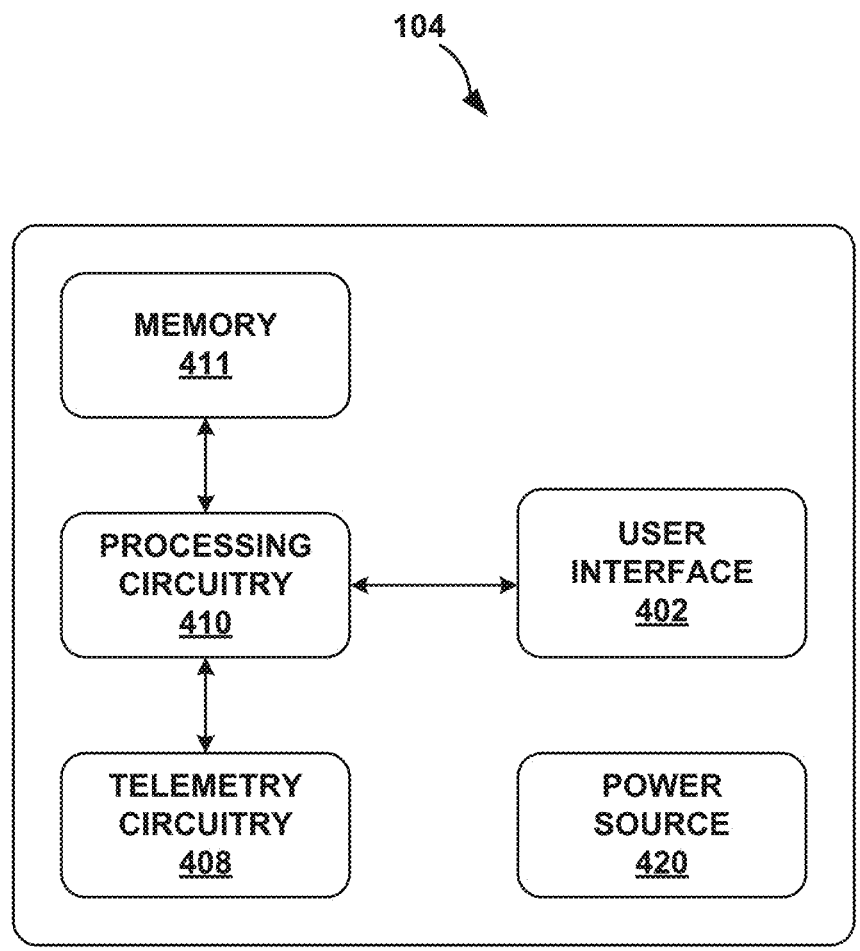
FIG. 4 is a block diagram of the external programmer of FIG. 1 for controlling delivery of electrical stimulation according to an example of the techniques of the disclosure.

FIG. 4 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 4, programmer 104 may include processing circuitry 410, memory 411, user interface 402, telemetry circuitry 408, and power source 420. Memory 411 may store instructions that, when executed by processing circuitry 410, cause processing circuitry 410 and external programmer 104 to provide the functionality ascribed to external programmer 104 throughout this disclosure. Each of these components, or modules, may include electrical circuitry that is configured to perform some or all of the functionality described herein. For example, processing circuitry 410 may include processing circuitry configured to perform the processes discussed with respect to processing circuitry 410.

In general, programmer 104 comprises any suitable arrangement of hardware, alone or in combination with software and/or firmware, to perform the techniques attributed to programmer 104, and processing circuitry 410, user interface 402, and telemetry circuitry 408 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 411, such as RAM, ROM, PROM, EPROM, EEPROM, flash memory, a hard disk, a CD-ROM, comprising executable instructions for causing the one or more processors to perform the actions attributed to them. Moreover, although processing circuitry 410 and telemetry circuitry 408 are described as separate modules, in some examples, processing circuitry 410 and telemetry circuitry 408 may be functionally integrated with one another. In some examples, processing circuitry 410 and telemetry circuitry 408 correspond to individual hardware units, such as ASICs, DSPs, FPGAs, or other hardware units.

Memory 411 (e.g., a storage device) may store instructions that, when executed by processing circuitry 410, cause processing circuitry 410 and programmer 104 to provide the functionality ascribed to programmer 104 throughout this disclosure. For example, memory 411 may include instructions that cause processing circuitry 410 to obtain a parameter set from memory or receive a user input and send a corresponding command to IMD 106, or instructions for any other functionality. In addition, memory 411 may include a plurality of programs, where each program includes a parameter set that defines stimulation therapy.

User interface 402 may include a button or keypad, lights, a speaker for voice commands, a display, such as a liquid crystal (LCD), light-emitting diode (LED), or organic light-emitting diode (OLED). In some examples the display may be a touch screen. User interface 402 may be configured to display any information related to the delivery of stimulation therapy, identified patient behaviors, sensed patient parameter values, patient behavior criteria, or any other such information. User interface 402 may also receive user input. The input may be, for example, in the form of pressing a button on a keypad or selecting an icon from a touch screen.

Telemetry circuitry 408 may support wireless communication between IMD 106 and programmer 104 under the control of processing circuitry 410. Telemetry circuitry 408 may also be configured to communicate with another computing device via wireless communication techniques, or direct communication through a wired connection. In some examples, telemetry circuitry 408 provides wireless communication via an RF or proximal inductive medium. In some examples, telemetry circuitry 408 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

In some examples, processing circuitry 410 of external programmer 104 defines the parameters of electrical stimulation therapy, stored in memory 411, for delivering adaptive DBS to patient 112. In one example, processing circuitry 410 of external programmer 104, via telemetry circuitry 408, issues commands to IMD 106 causing IMD 106 to deliver electrical stimulation therapy via electrodes 116, 118 via leads 114.

In one or more examples, programmer 104 may be configured to perform one or more of the example techniques described in this disclosure. For instance, processing circuitry 410 may be configured to perform any of the example operations described above with respect to processing circuitry 210. For example, processing circuitry 410 may be configured to configure electrical stimulation information 214 with one or more programs that instruct IMD 106 to output electrical signal levels using one or more of bursts of pulses, interleaved pulses, or concurrent pulses.

Figure 5:
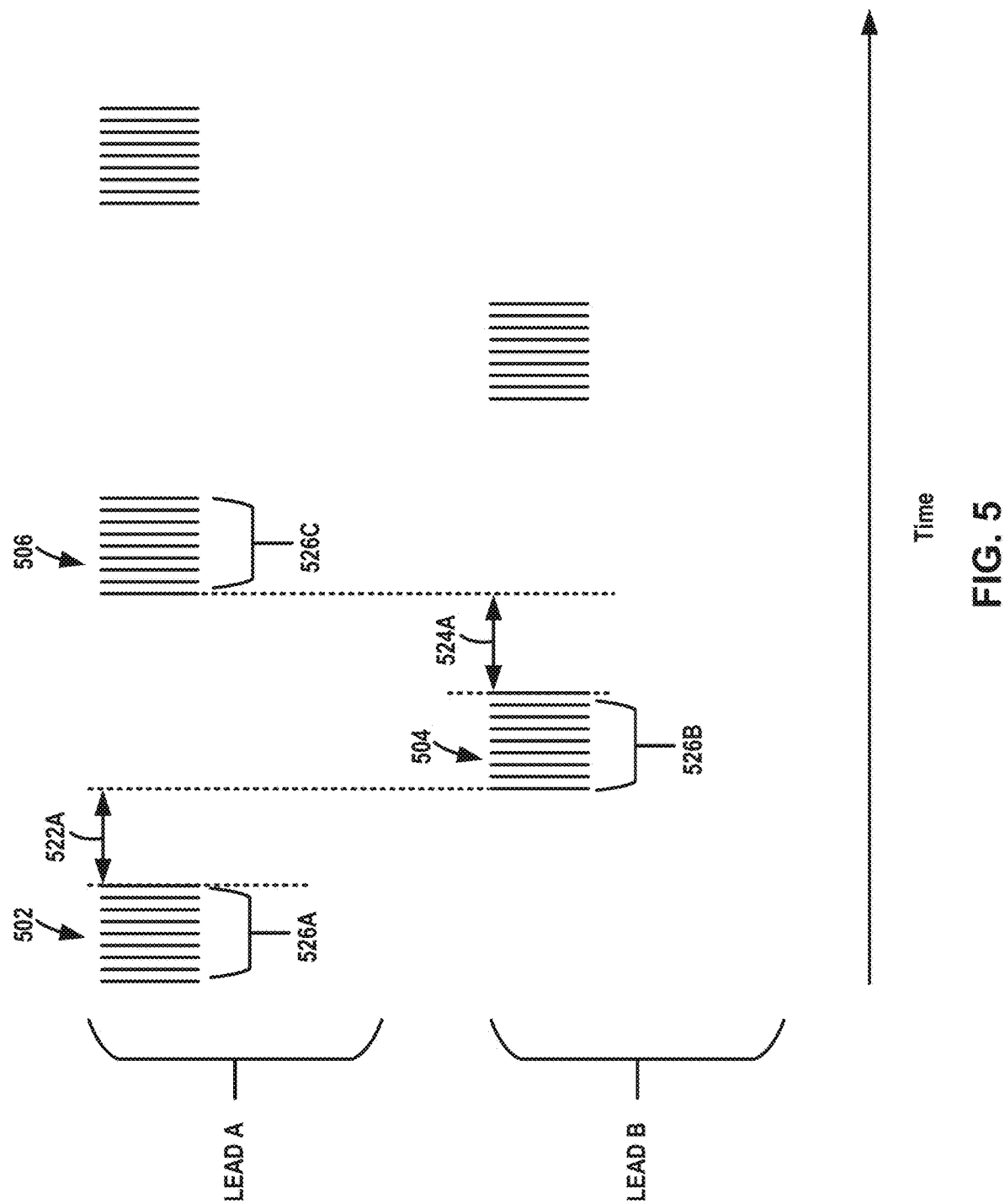
FIG. 5 is a conceptual diagram of providing electrical stimulation using bursts of pulses that have a constant duration according to an example of the techniques of the disclosure.

FIG. 5 is a conceptual diagram of providing electrical stimulation using a first burst of pulses 502 and a second burst of pulses 504 that have a constant duration according to an example of the techniques of the disclosure. For example, a medical device (e.g., processing circuitry 210) may generate first burst of pulses 502 at lead A (e.g., one or more of electrodes 116 of lead 114A) and a second burst of pulses 504 at lead B (e.g., one or more of electrodes 118 of lead 114B) after generating the first burst of pulses 502.

As shown, first burst of pulses 502 may comprise a first number of pulses (e.g., 9) equal to a second number (e.g., 9) of pulses of second burst of pulses 504. While the example of FIG. 5 illustrates first burst of pulses 502 and second burst of pulses 504 as comprising 9 pulses, first burst of pulses 502 and/or second burst of pulses 504 may comprise less than 9 pulses or more than 9 pulses. In some examples, first burst of pulses 502 may comprise a first duration 526A that corresponds to (e.g., is equal to) a second duration 526B of second burst of pulses 504.

In the example of FIG. 5, a first electrical signal comprises a third plurality of pulses that form a third burst of pulses 506. In the example of FIG. 5, first burst of pulses 502 may comprise a first number of pulses (e.g., 9 pulses) that is equal to a third number of pulses (e.g., 9 pulses) of third burst of pulses 506. In some examples, first duration 526A may correspond with (e.g., be equal to) a third duration 526C of third burst of pulses 506. In the example of FIG. 5, a delay 522A between first burst of pulses 502 and second burst of pulses 504 may be equal to a delay 524A between second burst of pulses 504 and third burst of pulses 506. Each one of pulses of one or more of first burst of pulses 502, second burst of pulses 504, or third burst of pulses 506 may comprise a sine wave or a cosine wave set to, for example, 130 Hz.

Figure 6:
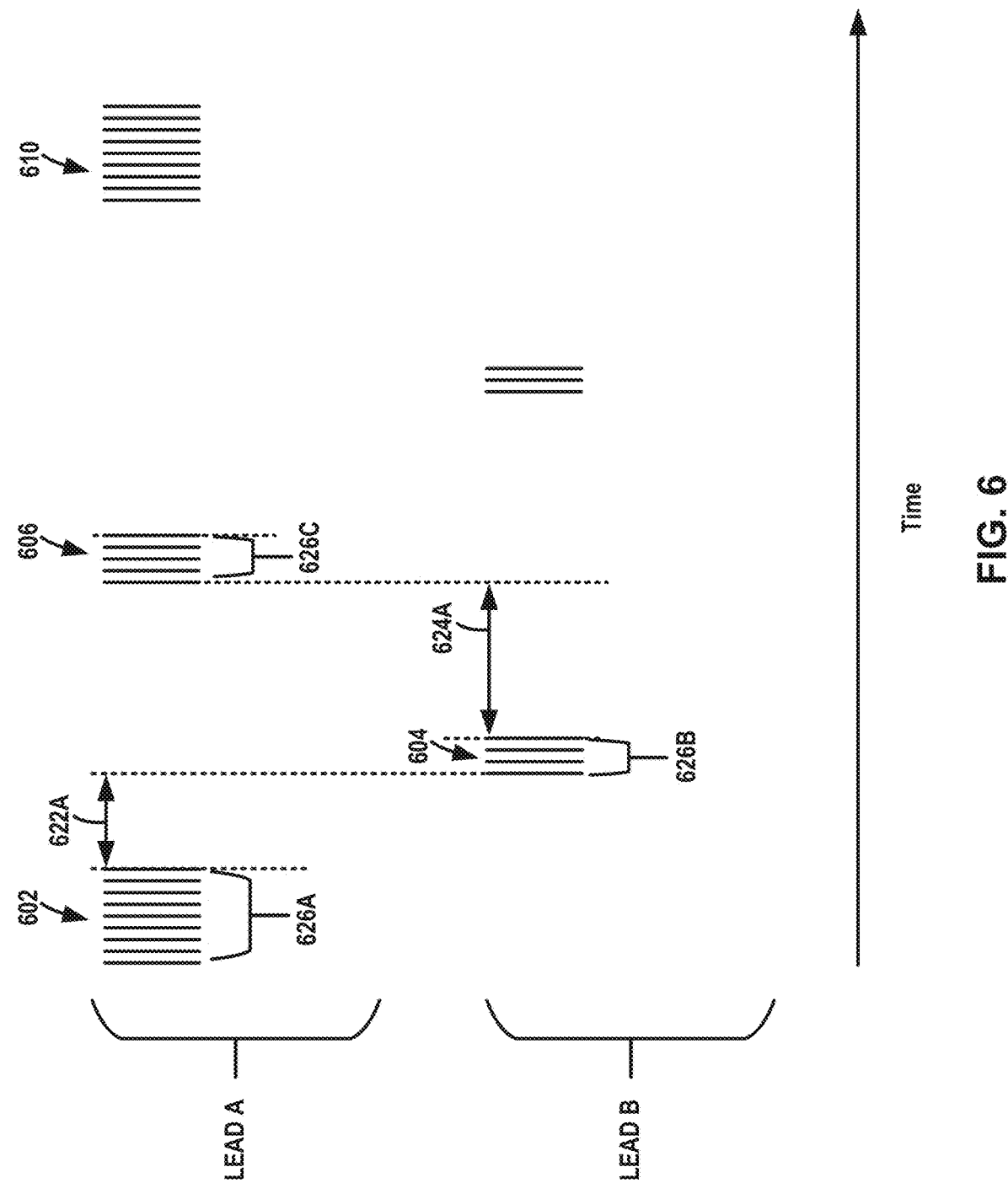
FIG. 6 is a conceptual diagram of providing electrical stimulation using bursts of pulses that have a variable duration according to an example of the techniques of the disclosure.

FIG. 6 is a conceptual diagram of providing electrical stimulation using a first burst of pulses 602 and a second burst of pulses 604 that have a variable duration according to an example of the techniques of the disclosure. For example, a medical device (e.g., processing circuitry 210) may generate first burst of pulses 602 at lead A (e.g., one or more of electrodes 116 of lead 114A) and a second burst of pulses 604 at lead B (e.g., one or more of electrodes 118 of lead 114B) after generating the first burst of pulses 602. While the example of FIG. 6 describes two leads, other examples may include more than 2 leads (e.g., 3 leads, 4 leads, 5 leads, or more than 5 leads).

As shown, first burst of pulses 602 may comprise a first number of pulses (e.g., 9) different from a second number (e.g., 4) of pulses of second burst of pulses 604. While the example of FIG. 6 illustrates first burst of pulses 602 as including 9 pulses, first burst of pulses 602 may include fewer than 9 pulses or more than 9 pulses. Similarly, while the example of FIG. 6 illustrates second burst of pulses 604 as including 3 pulses, second burst of pulses 604 may include fewer than 3 pulses or more than 3 pulses. In some examples, first burst of pulses 602 may comprise a first duration 626A that is different from a second duration 626B of second burst of pulses 604.

In the example of FIG. 6, a first electrical signal comprises a third plurality of pulses that form a third burst of pulses 606. In the example of FIG. 6, first burst of pulses 602 may comprise a first number of pulses (e.g., 9) that is different than a third number of pulses (e.g., 5 pulses) of third burst of pulses 606. In some examples, first duration 626A may be different from a third duration 626C of third burst of pulses 606. In the example of FIG. 6, a delay 622A between first burst of pulses 602 and second burst of pulses 604 may be different form a delay 624A between second burst of pulses 604 and third burst of pulses 606. Each one of pulses of one or more of first burst of pulses 602, second burst of pulses 604, or third burst of pulses 606 may comprise a sine wave or a cosine wave set to, for example, 130 Hz.

Figure 7:
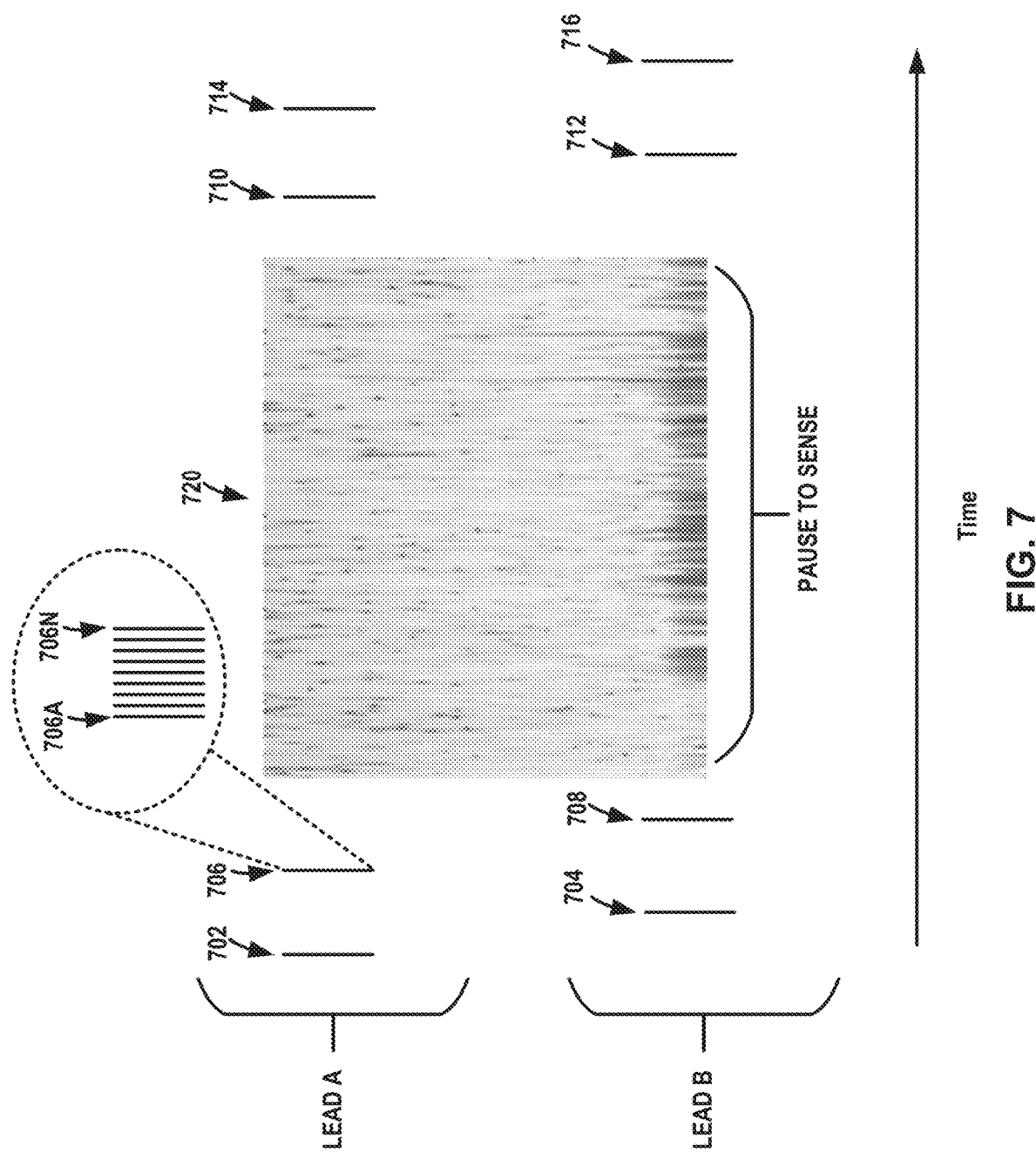
FIG. 7 is a conceptual diagram of providing electrical stimulation using bursts of pulses with a pause to sense operation according to an example of the techniques of the disclosure.

FIG. 7 is a conceptual diagram of providing electrical stimulation using bursts of pulses 702-716 with a pause to sense operation 720 according to an example of the techniques of the disclosure. As shown, each burst of pulse of bursts of pulses 702-716 may include one or more pulses. For example, burst of pulse 706 may include pulses 706A-706N.

For example, processing circuitry 210, with sensing circuitry 204, may sense one or more patient parameters while pausing the first electrical signal and the second electrical signal (e.g., delaying output of bursts of pulses 710-716). In this example, processing circuitry 210 may generate the first electrical signal (e.g., bursts of pulses 710, 714), generate the second electrical signal (e.g., bursts of pulses 712, 716), or generate both the first electrical signal and the second electrical signal based on the one or more patient parameters. For example, processing circuitry 210 may use LFP or accelerometer information to change and/or adapt the electrical stimulation, e.g., symmetric to variable.

Figure 8:
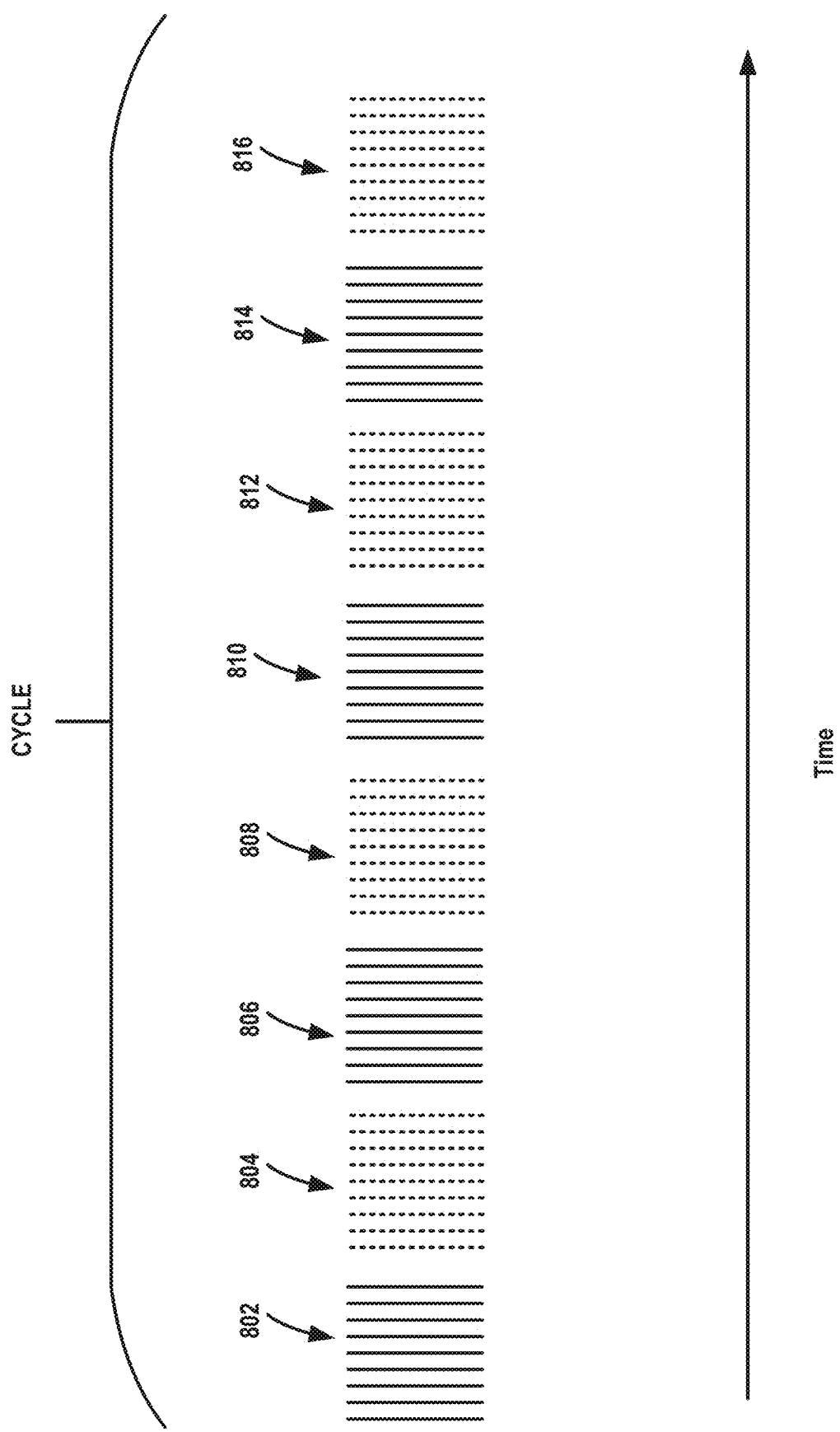
FIG. 8 is a conceptual diagram of a cycle for providing electrical stimulation using bursts of pulses according to an example of the techniques of the disclosure.

FIG. 8 is a conceptual diagram of a cycle for providing electrical stimulation using bursts of pulses 802-816 according to an example of the techniques of the disclosure. In this example, a medical device (e.g., processing circuitry 210) may generate burst of pulses 806 at lead B (e.g., one or more of electrodes 118 of lead 114B) after generating burst of pulses 804 at lead A (e.g., one or more of electrodes 116 of lead 114A), generate burst of pulses 808 at lead B after generating burst of pulses 806 at lead A, and so on. While the example of FIG. 8 illustrates 8 bursts of pulses in a cycle, a cycle may include less than 8 bursts of pulses or more than 8 bursts of pulses.

Figure 9:
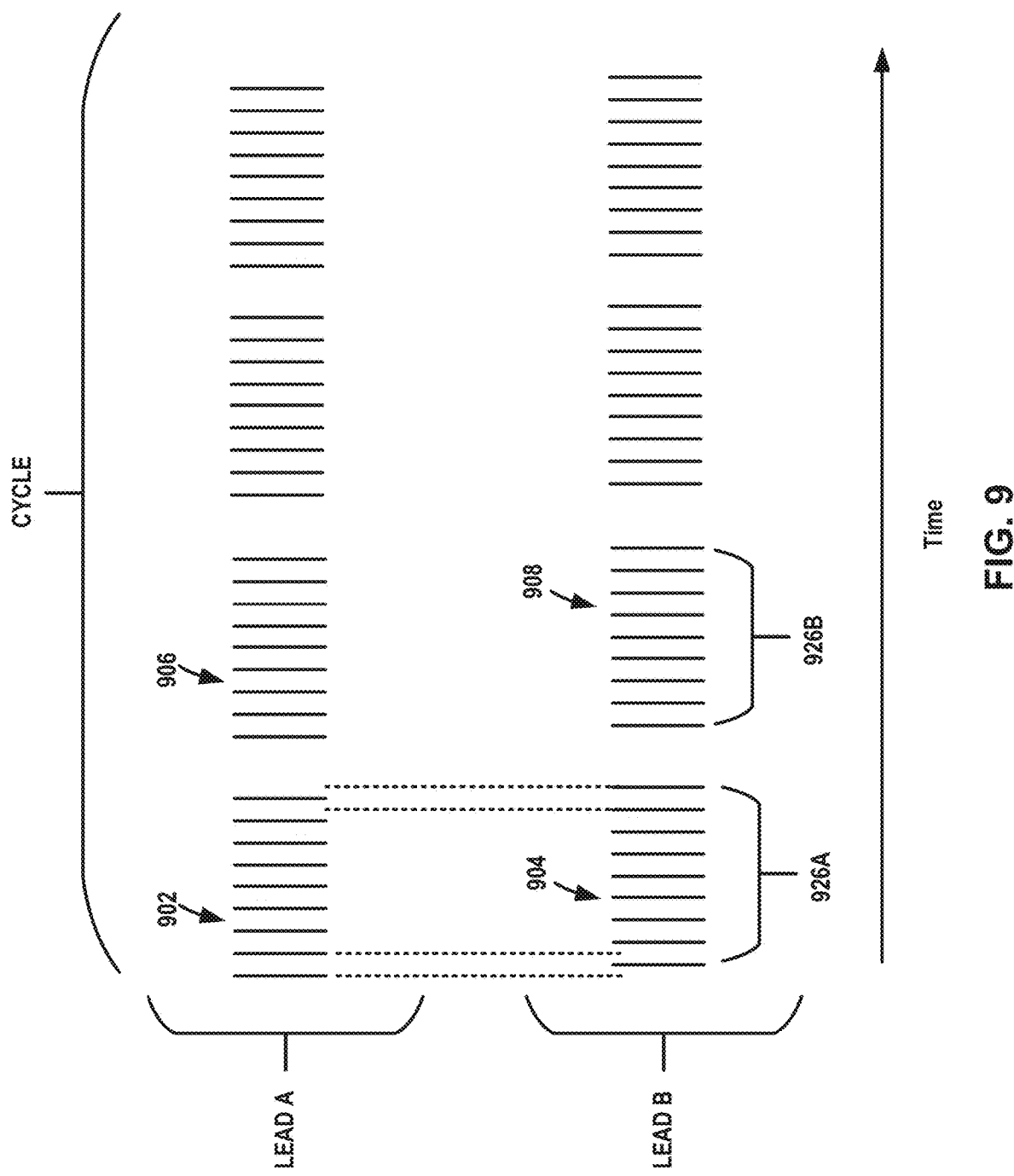
FIG. 9 is a conceptual diagram of providing electrical stimulation using a first portion of a plurality of interleaved pulses and a second portion of the plurality of interleaved pulses that have a constant duration according to an example of the techniques of the disclosure.

FIG. 9 is a conceptual diagram of providing electrical stimulation using a first portion 902 of a plurality of interleaved pulses and a second portion 904 of the plurality of interleaved pulses that have a constant duration according to an example of the techniques of the disclosure. For example, a medical device (e.g., processing circuitry 210) may generate first portion 902 of a plurality of interleaved pulses at lead A (e.g., one or more of electrodes 116 of lead 114A) and second portion 904 of a plurality of interleaved pulses at lead B (e.g., one or more of electrodes 118 of lead 114B).

As shown, first portion 902 of a plurality of interleaved pulses may comprise a first number of pulses (e.g., 9) equal to a second number (e.g., 9) of pulses of second portion 904 of the plurality of interleaved pulses. While the example of FIG. 9 illustrates first portion 902 of a plurality of interleaved pulses and second portion 904 of a plurality of interleaved pulses as comprising 9 pulses, first portion 902 of a plurality of interleaved pulses and/or second portion 904 of a plurality of interleaved pulses may comprise less than 9 pulses or more than 9 pulses.

In the example of FIG. 9, the first electrical signal comprises first portion 906 of a second plurality of interleaved pulses and the second electrical signal comprises second portion 908 of the second plurality of interleaved pulses. In the example of FIG. 9, first portion 902 of the first plurality of interleaved pulses may comprise a first number of pulses (e.g., 9 pulses) that is equal to a third number of pulses (e.g., 9 pulses) of first portion 906 of the second plurality of interleaved pulses. In some examples, first duration 926A may correspond with (e.g., be equal to) a second duration 926B of first portion 906 of the second plurality of interleaved pulses. Each one of pulses of one or more of first portion 902 and/or second portion 904 of the second plurality of interleaved pulses, or first portion 906 and/or second portion 908 of the second plurality of interleaved pulses may comprise a sine wave or a cosine wave set to, for example, 130 Hz.

Figure 10:
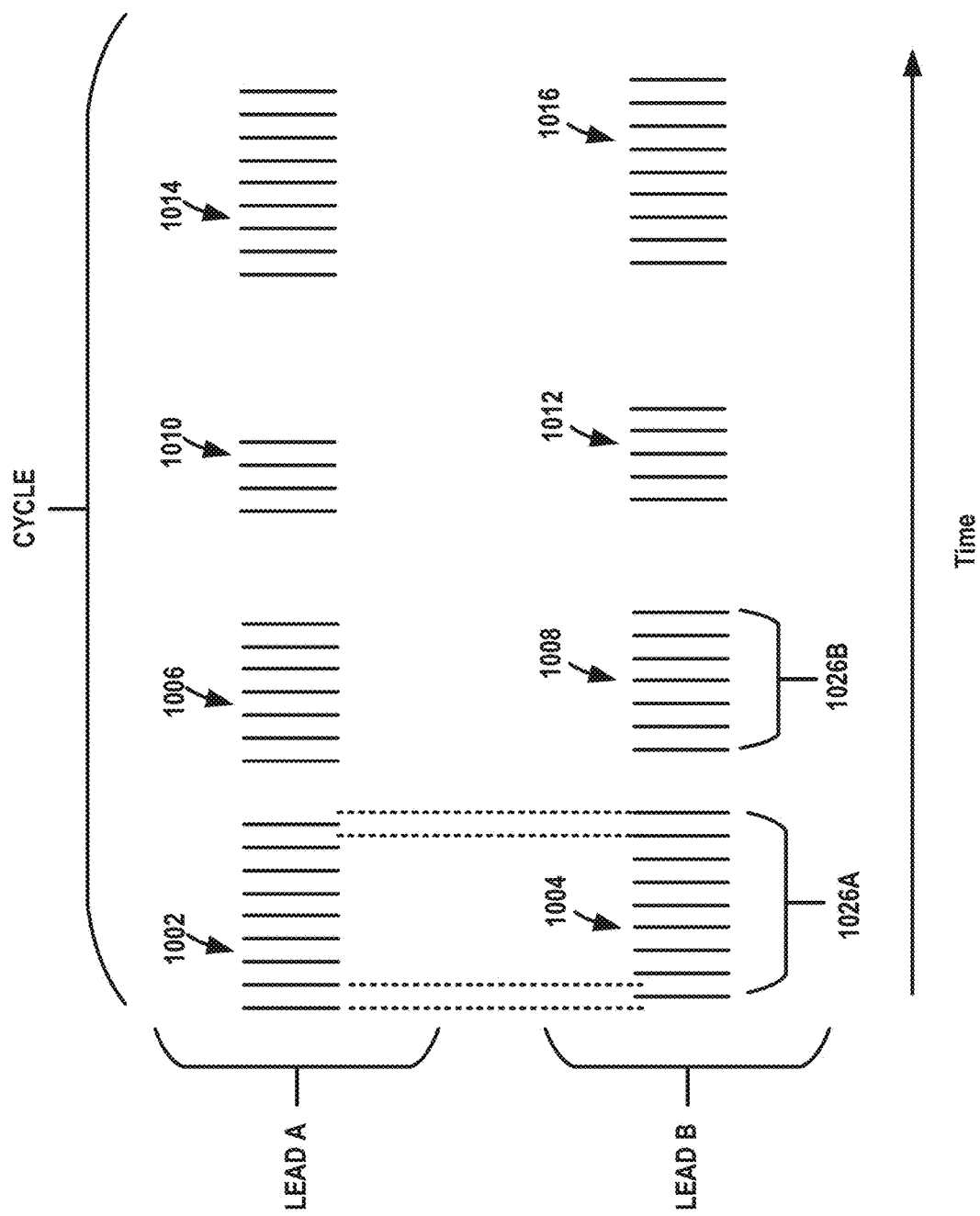
FIG. 10 is a conceptual diagram of providing electrical stimulation using a first portion of a plurality of interleaved pulses and a second portion of the plurality of interleaved pulses that have a variable duration according to an example of the techniques of the disclosure.

FIG. 10 is a conceptual diagram of providing electrical stimulation using a first portion 1002 of a plurality of interleaved pulses and a second portion 1004 of the plurality of interleaved pulses that have a variable duration according to an example of the techniques of the disclosure. For example, a medical device (e.g., processing circuitry 210) may generate first portion 1002 of a plurality of interleaved pulses at lead A (e.g., one or more of electrodes 116 of lead 114A) and second portion 1004 of a plurality of interleaved pulses at lead B (e.g., one or more of electrodes 118 of lead 114B).

As shown, first portion 1002 of a plurality of interleaved pulses may comprise a first number of pulses (e.g., 9) equal to a second number (e.g., 9) of pulses of second portion 1004 of a plurality of interleaved pulses. While the example of FIG. 10 illustrates first portion 1002 of the plurality of interleaved pulses and second portion 1004 of a plurality of interleaved pulses as comprising 9 pulses, first portion 1002 of a plurality of interleaved pulses and/or second portion 1004 of a plurality of interleaved pulses may comprise less than 9 pulses or more than 9 pulses.

In the example of FIG. 10, the first electrical signal comprises first portion 1006 of the second plurality of interleaved pulses and the second electrical signal comprises second portion 1008 of the second plurality of interleaved pulses. In the example of FIG. 10, first portion 1002 of the first plurality of interleaved pulses may comprise a first number of pulses (e.g., 9 pulses) that is different than a third number of pulses (e.g., 7 pulses) of first portion 1006 of the second plurality of interleaved pulses. In some examples, first duration 1026A may be different (e.g., shorter or longer) than a second duration 1026B of first portion 1006 of the second plurality of interleaved pulses. Each one of pulses of one or more of first portion 1002 and/or second portion 1004 of the second plurality of interleaved pulses, or first portion 1006 and/or second portion 1008 of the second plurality of interleaved pulses may comprise a sine wave or a cosine wave set to, for example, 130 Hz.

Figure 11:
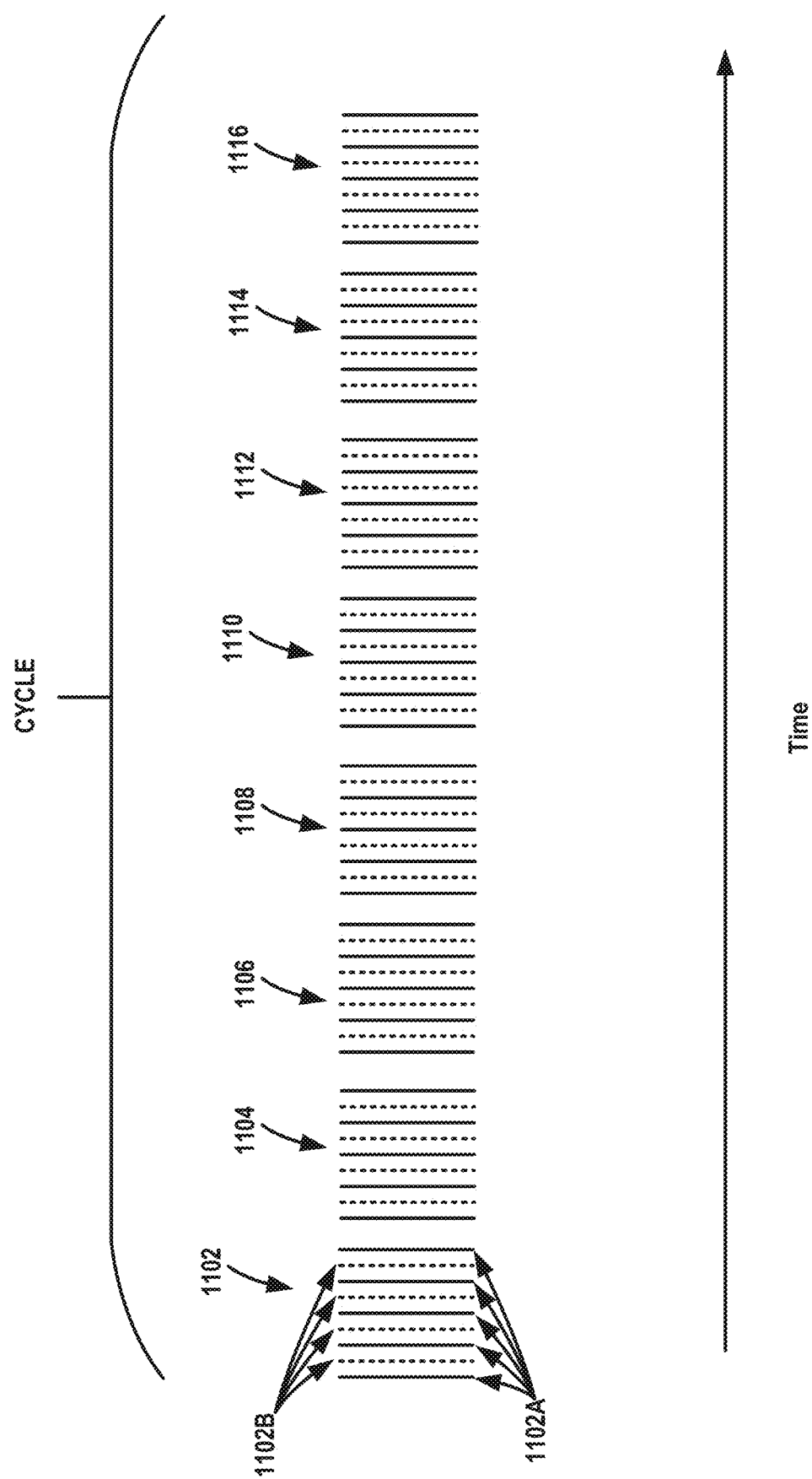
FIG. 11 is a conceptual diagram of a cycle for providing electrical stimulation using interleaved pulses according to an example of the techniques of the disclosure.

FIG. 11 is a conceptual diagram of a cycle for providing electrical stimulation using interleaved pulses 1102-1116 according to an example of the techniques of the disclosure. In this example, a medical device (e.g., processing circuitry 210) may generate interleaved pulses 1102-1116. For example, a medical device (e.g., processing circuitry 210) may generate first portion 1102A of interleaved pulses 1102 at lead A (e.g., one or more of electrodes 116 of lead 114A) and second portion 1102B of interleaved pulses 1102 at lead B (e.g., one or more of electrodes 118 of lead 114B). While the example of FIG. 11 illustrates 8 bursts of pulses in a cycle, a cycle may include less than 8 bursts of pulses or more than 8 bursts of pulses.

Figure 12:
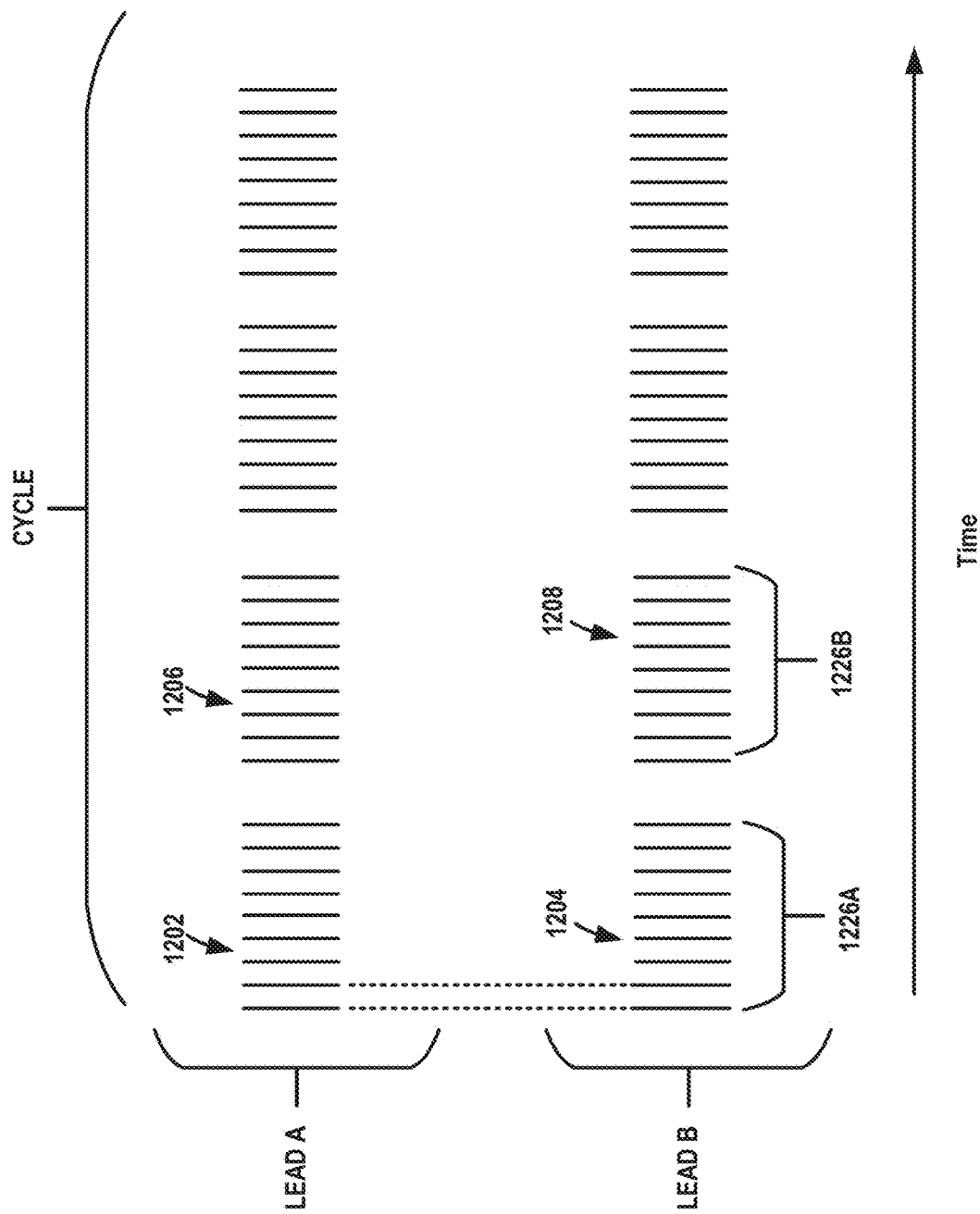
FIG. 12 is a conceptual diagram of providing electrical stimulation using a first portion of a plurality of concurrent pulses and a second portion of the plurality of concurrent pulses that have a constant duration according to an example of the techniques of the disclosure.

FIG. 12 is a conceptual diagram of providing electrical stimulation using a first portion 1202 of a plurality of concurrent pulses and a second portion 1204 of the plurality of concurrent pulses that have a constant duration according to an example of the techniques of the disclosure. For example, a medical device (e.g., processing circuitry 210) may generate first portion 1202 of a plurality of concurrent pulses at lead A (e.g., one or more of electrodes 116 of lead 114A) and second portion 1204 of a plurality of concurrent pulses at lead B (e.g., one or more of electrodes 118 of lead 114B).

As shown, first portion 1202 of the plurality of concurrent pulses may comprise a first number of pulses (e.g., 9) equal to a second number (e.g., 9) of pulses of second portion 1204 of the plurality of concurrent pulses. While the example of FIG. 12 illustrates first portion 1202 of the plurality of concurrent pulses and second portion 1204 of a plurality of concurrent pulses as comprising 9 pulses, first portion 1202 of a plurality of concurrent pulses and/or second portion 1204 of a plurality of concurrent pulses may comprise less than 9 pulses or more than 9 pulses.

In the example of FIG. 12, the first electrical signal comprises first portion 1206 of a second plurality of concurrent pulses and the second electrical signal may comprise second portion 1208 of the second plurality of concurrent pulses. In the example of FIG. 12, first portion 1206 of the second plurality of concurrent pulses may comprise a first number of pulses (e.g., 9 pulses) that is equal to a third number of pulses (e.g., 9 pulses) of first portion 1206 of the second plurality of concurrent pulses. In some examples, first duration 1226A may correspond with (e.g., be equal to) a second duration 1226B of first portion 906 of the second plurality of concurrent pulses. Each one of pulses of one or more of first portion 1202 and/or second portion 904 of the second plurality of concurrent pulses, or first portion 906 and/or second portion 908 of the second plurality of concurrent pulses may comprise a sine wave or a cosine wave set to, for example, 130 Hz.

Figure 13:
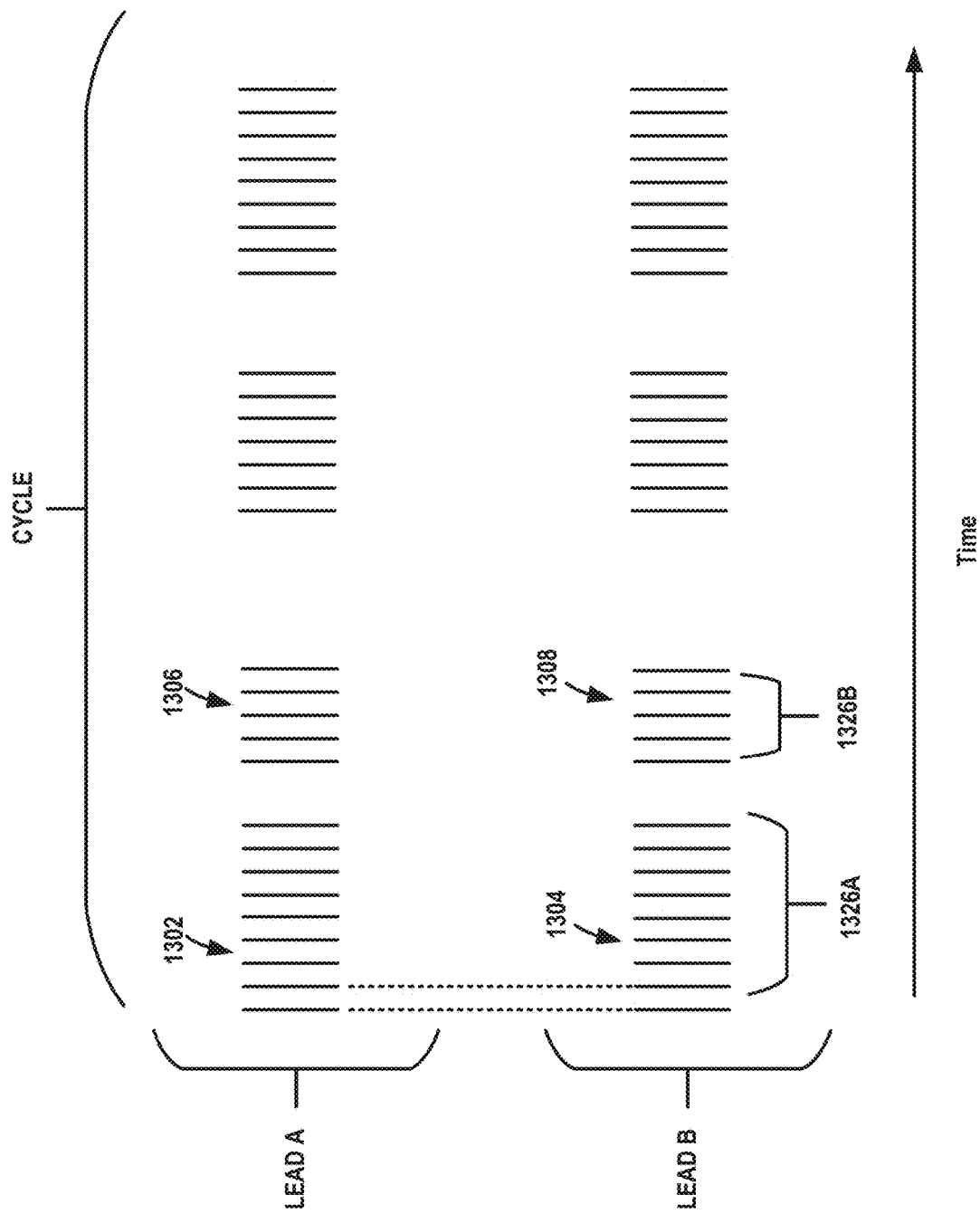
FIG. 13 is a conceptual diagram of providing electrical stimulation using a first portion of a plurality of concurrent pulses and a second portion of the plurality of concurrent pulses that have a variable duration according to an example of the techniques of the disclosure.

FIG. 13 is a conceptual diagram of providing electrical stimulation using a first portion 1302 of a plurality of concurrent pulses and a second portion 1304 of the plurality of concurrent pulses that have a variable duration according to an example of the techniques of the disclosure. For example, a medical device (e.g., processing circuitry 210) may generate first portion 1302 of a plurality of concurrent pulses at lead A (e.g., one or more of electrodes 116 of lead 114A) and second portion 1304 of a plurality of concurrent pulses at lead B (e.g., one or more of electrodes 118 of lead 114B).

As shown, first portion 1302 of a plurality of concurrent pulses may comprise a first number of pulses (e.g., 9) equal to a second number (e.g., 9) of pulses of second portion 1304 of a plurality of concurrent pulses. While the example of FIG. 13 illustrates first portion 1302 of the plurality of concurrent pulses and second portion 1304 of a plurality of concurrent pulses as comprising 9 pulses, first portion 1302 of a plurality of concurrent pulses and/or second portion 1304 of a plurality of concurrent pulses may comprise less than 9 pulses or more than 9 pulses.

In the example of FIG. 13, the first electrical signal comprises first portion 1306 of the second plurality of concurrent pulses and the second electrical signal comprises second portion 1308 of the second plurality of concurrent pulses. In the example of FIG. 13, first portion 1302 of the first plurality of concurrent pulses may comprise a first number of pulses (e.g., 9 pulses) that is different than a third number of pulses (e.g., 5 pulses) of first portion 1306 of the second plurality of concurrent pulses. In some examples, first duration 1326A may be different than a second duration 1326B of first portion 1306 of the second plurality of concurrent pulses. Each one of pulses of one or more of first portion 1302 and/or second portion 1304 of the second plurality of concurrent pulses, or first portion 1306 and/or second portion 1308 of the second plurality of concurrent pulses may comprise a sine wave or a cosine wave set to, for example, 130 Hz.

Figure 14:
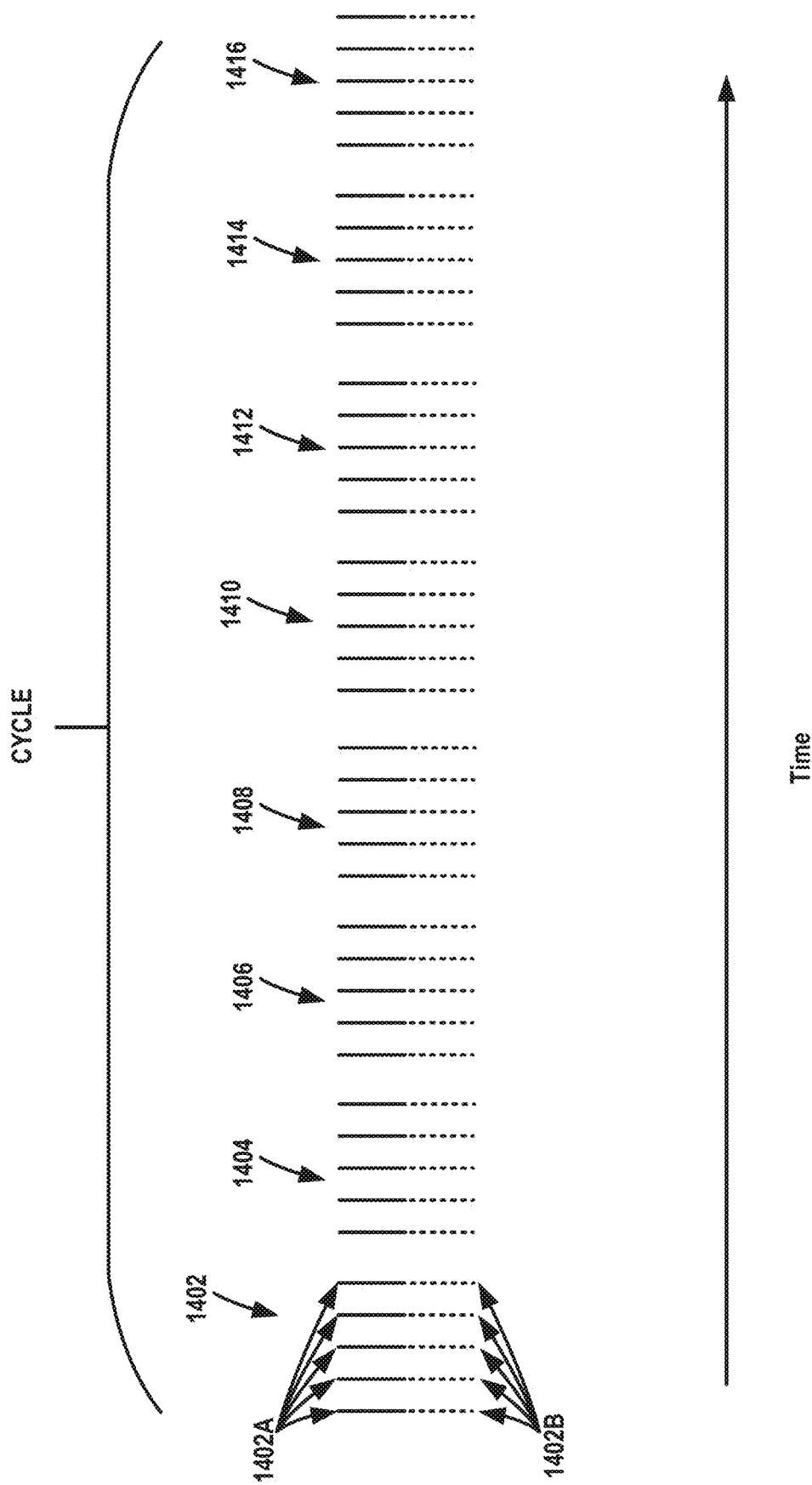
FIG. 14 is a conceptual diagram of a cycle for providing electrical stimulation using a first portion of a plurality of concurrent pulses and a second portion of the plurality of concurrent pulses according to an example of the techniques of the disclosure.

FIG. 14 is a conceptual diagram of a cycle for providing electrical stimulation using a concurrent pulses 1402-1416 according to an example of the techniques of the disclosure. In this example, a medical device (e.g., processing circuitry 210) may generate concurrent pulses 1402-1416. For example, a medical device (e.g., processing circuitry 210) may generate first portion 1402A of concurrent pulses 1402 at lead A (e.g., one or more of electrodes 116 of lead 114A) and second portion 1402B of concurrent pulses 1402 at lead B (e.g., one or more of electrodes 118 of lead 114B). While the example of FIG. 14 illustrates 8 bursts of pulses in a cycle, a cycle may include less than 8 bursts of pulses or more than 8 bursts of pulses.

Figure 15:
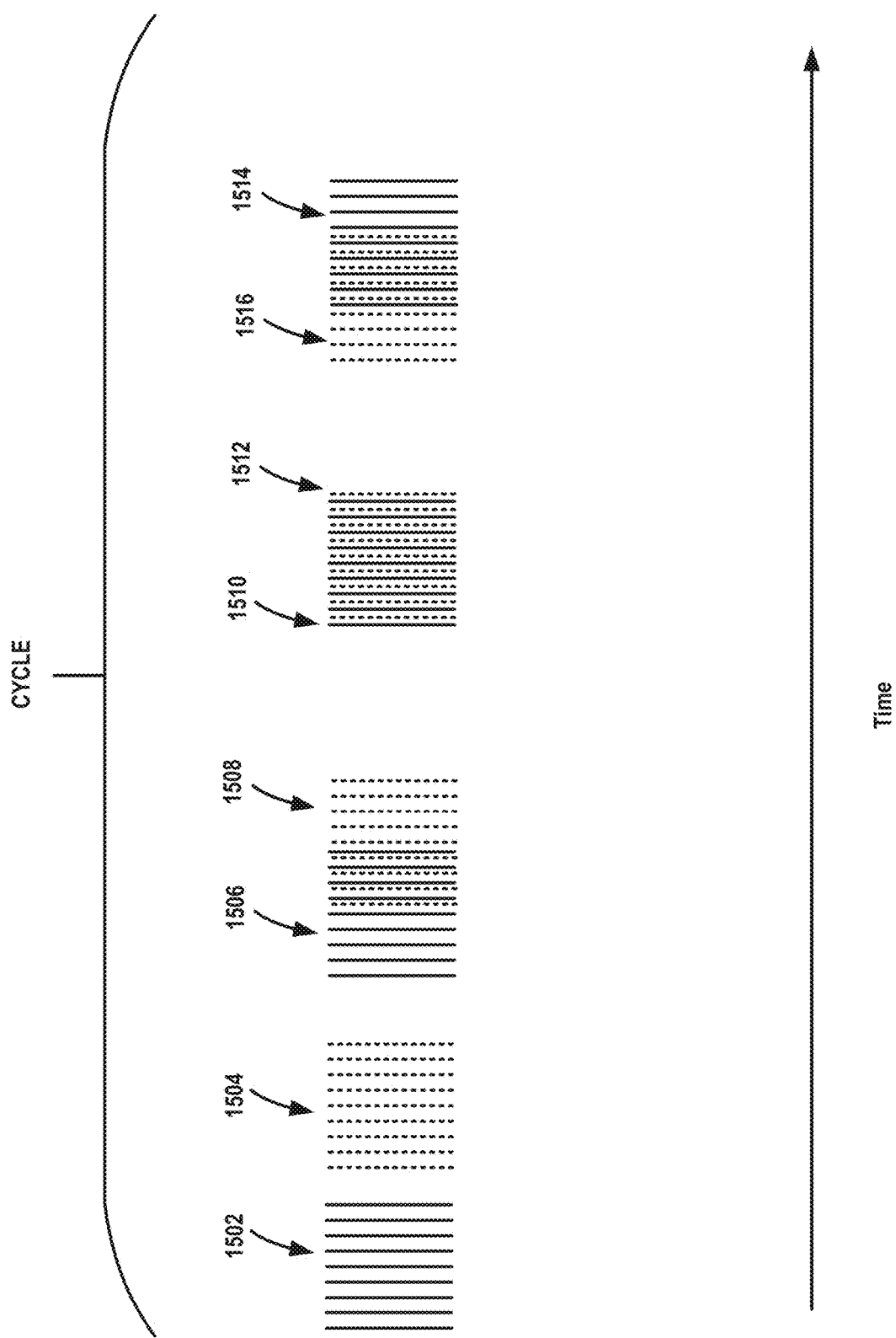
FIG. 15 is a conceptual diagram of a cycle for providing electrical stimulation using pulses that have a different frequencies according to an example of the techniques of the disclosure.

FIG. 15 is a conceptual diagram of a cycle for providing electrical stimulation using pulses that have a different frequencies according to an example of the techniques of the disclosure. In this example, a medical device (e.g., processing circuitry 210) may generate pulses 1502-1516 where a first burst of pulses 1502, 1506, 1510, and 1514 "slide" through time from a second burst of pulses 1504, 1508, 1512, and 1516 at different rates leading to intervals where pulses 1510 and 1512 are interleaved (e.g., FIG. 11) but also time intervals where they do not overlap, and thus behave more like the example of FIG. 8. For instance, the medical device may generate first burst of pulses 1502, 1506, 1510, and 1514 with a first period that is longer than a second period for generating second burst of pulses 1504, 1508, 1512, and 1516. In some instances, the medical device may generate first burst of pulses 1502, 1506, 1510, and 1514 with a first burst frequency that is smaller than a second burst frequency for generating second burst of pulses 1504, 1508, 1512, and 1516. As used herein, burst frequency may refer to a rate at which pulses are repeated in a burst of pulses. In contrast, each pulse may comprise a pulse frequency that indicates an electrical frequency of the pulse (e.g., a sine wave at 130 Hz or a cosine wave at 130 Hz). A medical device (e.g., processing circuitry 210) may generate first burst of pulses 1502, 1506, 1510, and 1514 at lead A (e.g., one or more of electrodes 116 of lead 114A) and second burst of pulses 1504, 1508, 1512, and 1516 at lead B (e.g., one or more of electrodes 118 of lead 114B). While the example of FIG. 15 illustrates 8 bursts of pulses in a cycle, a cycle may include less than 8 bursts of pulses or more than 8 bursts of pulses.

Figure 16:
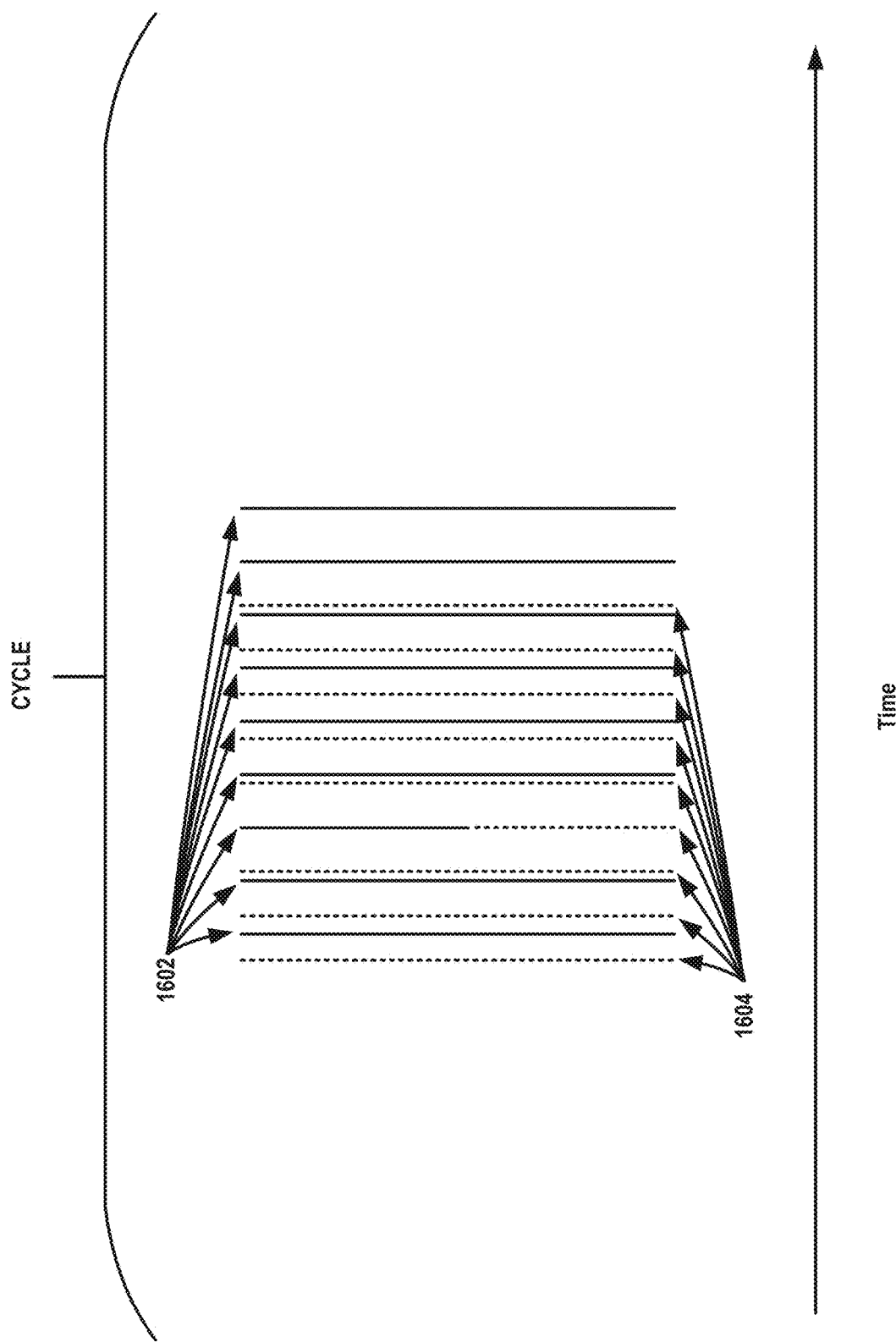
FIG. 16 is a conceptual diagram of an example shift of pulses that have a different frequencies according to an example of the techniques of the disclosure.

FIG. 16 is a conceptual diagram of an example shift of pulses that have a different frequencies according to an example of the techniques of the disclosure. In this example, a medical device (e.g., processing circuitry 210) may generate a burst of pulses 1602 that slide through time from burst of pulses 1604 at different rates leading to intervals where they overlap and thus are interleaved (e.g., FIG. 11) but also time intervals where they do not overlap, and thus behave more like the example of FIG. 8. For instance, the medical device may generate burst of pulses 1602 with a first period that is longer than a second period for generating burst of pulses 1604. In some instances, the medical device may generate burst of pulses 1602 with a first burst frequency that is smaller than a second burst frequency for generating burst of pulses 1604. A medical device (e.g., processing circuitry 210) may generate first pulses 1602 at lead A (e.g., one or more of electrodes 116 of lead 114A) and second pulses 1604 lead B (e.g., one or more of electrodes 118 of lead 114B). While the example of FIG. 16 illustrates 8 bursts of pulses in a cycle, a cycle may include less than 8 bursts of pulses or more than 8 bursts of pulses.

Figure 17:
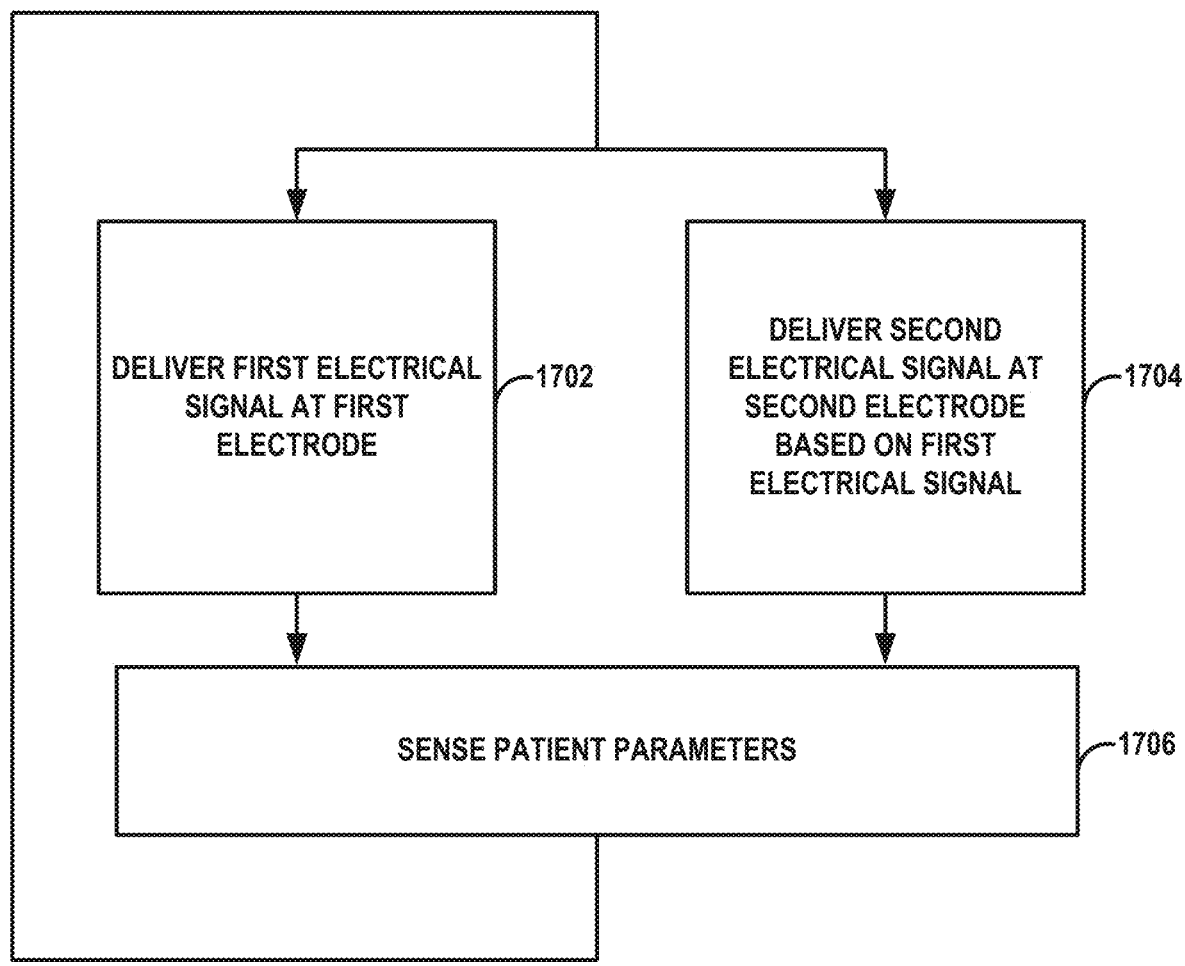
FIG. 17 is a flowchart illustrating an example operation for delivering a first electrical signal and a second electrical signal to desynchronize regions of a brain of a patient in accordance with techniques of the disclosure.

FIG. 17 is a flowchart illustrating an example operation for delivering a first electrical signal and a second electrical signal to desynchronize regions of a brain of a patient in accordance with techniques of the disclosure. For ease of description, the example of FIG. 17 is described with respect to processing circuitry 210 of IMD 106, but may be performed by processing circuitry 410 of programmer 104 or possibly a combination of both.

Processing circuitry 210 may be configured to deliver a first electrical signal at a first electrode (1702) and deliver a second electrical signal at a second electrode (1704). The first electrode may be implanted to apply electrical stimulation to a first region (e.g., a first part of a first hemisphere) of a brain of a patient. Similarly, the second electrode may be implanted to apply electrical stimulation to a second region (e.g., a second part of a first hemisphere or a second hemisphere) of a brain of a patient.

For example, processing circuitry 210 may be configured to apply a first burst of pulses to a first region of the brain and apply a second burst of pulses to a second region of the brain after applying the first burst of pulses to the first region of the brain. For instance, processing circuitry 210 may generate the first electrical signal to comprise a first plurality of pulses that form a first burst of pulses. In this example, processing circuitry 210 may generate the second electrical signal to comprise a second plurality of pulses that form a second burst of pulses after generating the first burst of pulses.

In some examples, processing circuitry 210 may be configured to apply a first portion of interleaved pulses to a first region of the brain and apply a second portion of the interleaved pulses to the second region of the brain. For example, processing circuitry 210 may generate the first portion of the plurality of interleaved pulses to comprise a first pulse and a third pulse. In this example, processing circuitry 210 may generate the second portion of the plurality of interleaved pulses to comprise a second pulse after the first pulse and before the third pulse and generate a fourth pulse after the third pulse.

Processing circuitry 210 may be configured to apply a first portion of concurrent pulses to a first region of the brain and apply a second portion of the concurrent pulses to the second region of the brain. For example, processing circuitry 210 may generate the first portion of the plurality of concurrent pulses to comprise a first pulse and a third pulse. In this example, processing circuitry 210 may generate the second portion of the plurality of concurrent pulses to comprise a second pulse concurrently with the first pulse (e.g., simultaneously or substantially simultaneously) and generate a fourth pulse concurrently with the third pulse.

Processing circuitry 210 may be configured to apply a first burst of pulses to a first region of the brain and apply a second burst of pulses to the second region of the brain. For instance, processing circuitry 210 may generate the first electrical signal to comprise a first plurality of pulses that form a first burst of pulses that are slide through time from the second burst of pulses at different rates leading to intervals where one or more pulses of the first burst of pulses are interleaved with the second burst of pulses and where one or more other pulses of the first burst of pulses do not overlap with the second burst of pulses (See FIGS. 15, 16).

Processing circuitry 210, with sensing circuitry 204, may sense patient parameters (1706) and the process repeats to 1502. For example, processing circuitry 210, with sensing circuitry 204, may sense one or more patient parameters while pausing the first electrical signal and the second electrical signal. Processing circuitry 210 may generate the first electrical signal, generate the second electrical signal, or generate both the first electrical signal and the second electrical signal based on the one or more patient parameters.

Configuring processing circuitry 210 to generate a first electrical signal and generate a second electrical signal based on the first electrical signal (e.g., using bursts of pulses, interleaved pulses, and/or concurrent pulses) to regions of the brain of a patient may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders. In this way, processing circuitry 210 may help to desynchronize regions of a brain of a patient, which may improve a therapy provided to the patient.

Figure 18:
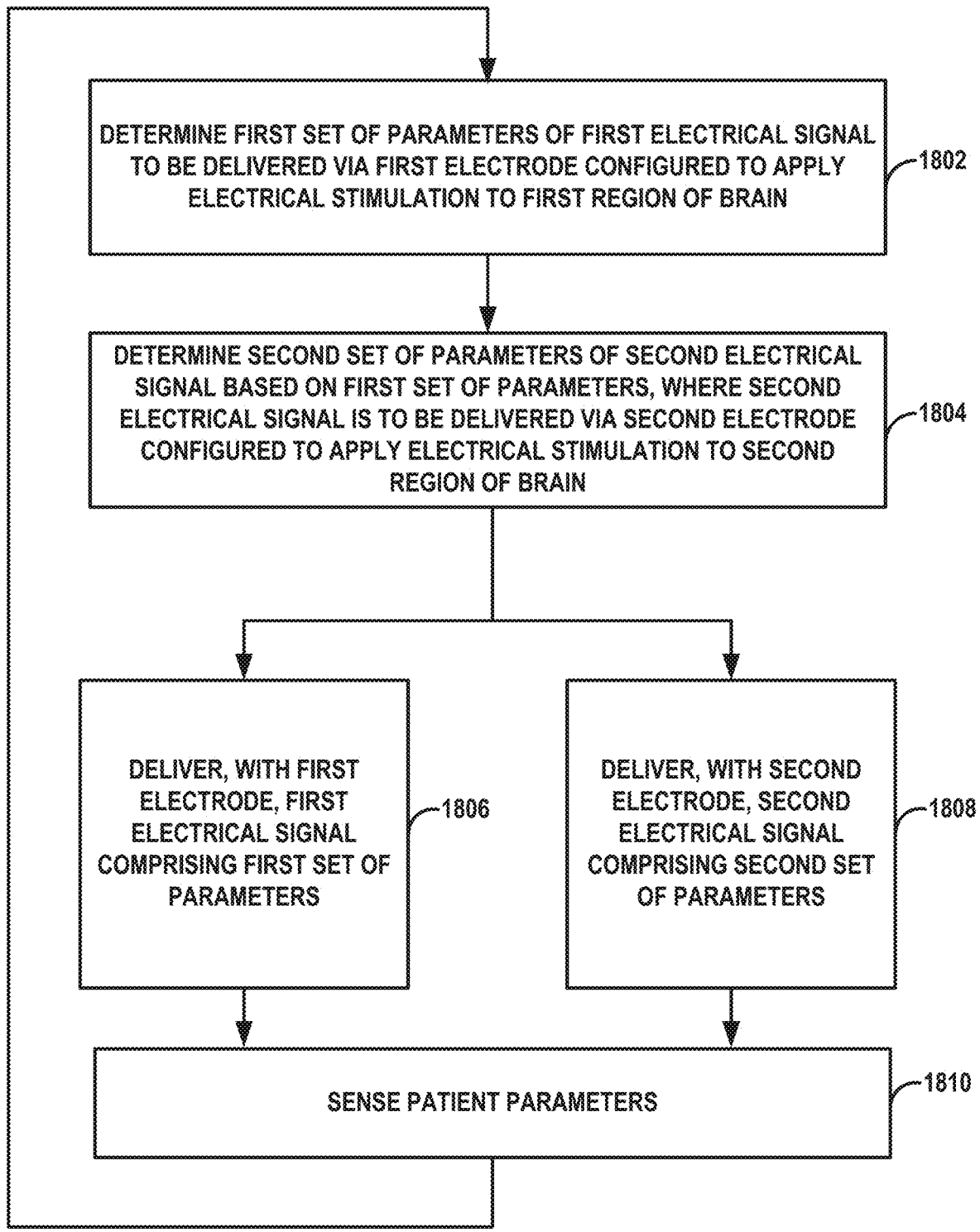
FIG. 18 is a flowchart illustrating an example operation for determining first electrical parameters of a first electrical signal and determining second electrical parameters of a second electrical signal to desynchronize regions of a brain of a patient in accordance with techniques of the disclosure.

FIG. 18 is a flowchart illustrating an example operation for determining first electrical parameters of a first electrical signal and determining second electrical parameters of a second electrical signal to desynchronize regions of a brain of a patient in accordance with techniques of the disclosure. For ease of description, the example of FIG. 18 is described with respect to processing circuitry 210 of IMD 106, but may be performed by processing circuitry 410 of programmer 104 or possibly a combination of both.

Processing circuitry 210 may be configured to determine a first set of parameters of a first electrical signal that is delivered via a first electrode configured to apply electrical stimulation to a first region of the brain (1802). For example, processing circuitry 210 may be configured to determine a first set of parameters of a first electrical signal that is delivered via electrode 116. Processing circuitry 210 may be configured to determine a second set of parameters of a second electrical signal based on the first set of parameters, where the second electrical signal is delivered via a second electrode configured to apply electrical stimulation to a second region of the brain (1804). For example, processing circuitry 210 may be configured to determine the second set of parameters of the second electrical signal that is delivered via electrode 118. Processing circuitry 210 may deliver, with the first electrode, the first electrical signal having the first set of parameters (1806) and may deliver, with the second electrode, the second electrical signal having the second set of parameters (1808).

For example, to determine the first set of parameters, processing circuitry 210 may determine a first plurality of pulses that form a first burst of pulses. For instance, processing circuitry 210 may select the first plurality of pulses that form the first burst of pulses from a pre-configured burst pattern. In this example, to determine the second set parameters, processing circuitry 210 may set a second plurality of pulses that form a second burst of pulses to occur after delivering the first burst of pulses. For instance, processing circuitry 210 may select the second plurality of pulses that form the second burst of pulses from the pre-configured burst pattern. In this way, the first electrical signal may deliver the first burst of pulses in a first region of a brain of patient 112 that is coordinated with the second electrical signal delivering the second burst of pulses in a second region of a brain of patient 112, which may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders.

For example, to determine the first set of parameters, processing circuitry 210 may determine a first portion of a plurality of interleaved pulses. For instance, processing circuitry 210 may select the first portion of a plurality of interleaved pulses from a pre-configured interleaved pattern. In this example, to determine the second set parameters, processing circuitry 210 may determine a second portion of the plurality of interleaved pulses. For instance, processing circuitry 210 may select the second portion of a plurality of interleaved pulses from the pre-configured interleaved pattern. The first portion of the plurality of interleaved pulses may comprise a first pulse and a third pulse and the second portion of the plurality of interleaved pulses may comprise a second pulse and a fourth pulse. In this instance, processing circuitry 210 may set the second pulse to occur after the first pulse and before the third pulse and setting the fourth pulse to occur after the third pulse. In this way, the first electrical signal may deliver the first portion of the plurality of interleaved pulses in a first region of a brain of the patient that is coordinated with the second electrical signal delivering the second portion of the plurality of interleaved pulses in a second region of a brain of the patient, which may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders.

To determine the first set of parameters, processing circuitry 210 may determine a first portion of a plurality of concurrent pulses. For instance, processing circuitry 210 may select the second portion of a plurality of concurrent pulses from the pre-configured concurrent pattern. In this example, to determine the second set parameters, processing circuitry 210 may determine a second portion of the concurrent of interleaved pulses to be delivered concurrently with the delivery of the first portion of the plurality of concurrent pulses. For instance, processing circuitry 210 may select the second portion of a plurality of concurrent pulses from the pre-configured concurrent pattern. In this way, the first electrical signal may deliver the first portion of the plurality of concurrent pulses in a first region of a brain of the patient that is coordinated with the second electrical signal delivering the second portion of the plurality of concurrent pulses in a second region of a brain of the patient, which may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders.

To determine the first set of parameters, processing circuitry 210 may determine a determine a first plurality of pulses that form a first burst of pulses. For instance, processing circuitry 210 may select the first plurality of pulses that form the first burst of pulses from a pre-configured burst pattern. In this example, to determine the second set parameters, processing circuitry 210 may set a second plurality of pulses that form a second burst of pulses such that a first pulse of the second burst of pulses overlaps with at least one pulse of the first burst of pulses and a second pulse of the second burst of pulses does not overlap with any pulse of the first burst of pulses (see FIGS. 15, 16). In some examples, to determine the second set parameters, processing circuitry 210 may set the second burst of pulses to comprise a second burst frequency that is different than a first burst frequency of the first burst of pulses. For instance, processing circuitry 210 may select the second plurality of pulses that form the second burst of pulses from the pre-configured burst pattern. In this way, the first electrical signal may deliver the first burst of pulses in a first region of a brain of patient 112 that is coordinated with the second electrical signal delivering the second burst of pulses in a second region of a brain of patient 112, which may help to desynchronize regions of a brain of a patient. Desynchronizing regions of a brain of a patient may help to reduce or eliminate one or more of movement disorders, neurodegenerative impairment, seizure disorders (e.g., epilepsy), mood disorders, or psychological disorders.

In some examples, processing circuitry 210 may adaptively determine the first set of parameters of a first electrical signal and/or the second set of parameters of a second electrical signal based on a physiology information. For instance, processing circuitry 210 may adaptively determine the first set of parameters of a first electrical signal and/or the second set of parameters of a second electrical signal based on one or more of a local field potentials (LFP) or a patient reported output (PRO). For example, processing circuitry 210 may determine, based on the LFP or PRO, the first plurality of pulses to form a first burst of pulses that occur before a second burst of pulses, a first burst of pulses that shift with a second burst of pulses), a first portion of interleaved pulses, or a first portion of a plurality of concurrent pulses. Similarly, processing circuitry 210 may determine, based on the LFP or PRO, the second plurality of pulses to form a second burst of pulses that occur after a first burst of pulses, a second burst of pulses that shift with the first burst of pulses), a second portion of interleaved pulses, or a second portion of a plurality of concurrent pulses.

Processing circuitry 210, with sensing circuitry 204, may sense patient parameters (1810) and the process may repeat to 1602. For example, processing circuitry 210, with sensing circuitry 204, may sense one or more patient parameters while pausing the first electrical signal and the second electrical signal. Processing circuitry 210 may generate the first electrical signal, generate the second electrical signal, or generate both the first electrical signal and the second electrical signal based on the one or more patient parameters.

For example, processing circuitry 210 may sense patient parameters while refraining from delivering the first electrical signal and the second electrical signal. In this example, processing circuitry 210 may determine whether the first region of the brain of a patient and a second region of the brain are overly synchronized based on the patient parameters. Processing circuitry 210 may continue to deliver the first electrical signal and the second electrical signal when the first region of the brain of a patient and a second region of the brain are overly synchronized. However, processing circuitry 210 may stop delivering the first electrical signal and the second electrical signal when the first region of the brain of a patient and a second region of the brain are not overly synchronized.

The following examples are a non-limiting list of clauses in accordance with one or more techniques of this disclosure.

Clause 1: A method for providing electrical stimulation to a brain of a patient, the method comprising: determining, with one or more processors, a first set of parameters of a first electrical signal that is delivered via a first electrode configured to apply electrical stimulation to a first region of the brain; determining, with the one or more processors, a second set of parameters of a second electrical signal based on the first set of parameters, wherein the second electrical signal is delivered via a second electrode configured to apply electrical stimulation to a second region of the brain; delivering, with the one or more processors and with the first electrode, the first electrical signal having the first set of parameters; and delivering, with the one or more processors and with the second electrode, the second electrical signal having the second set of parameters.

Clause 2. The method of clause 1, wherein determining the first set of parameters of the first electrical signal comprises determining a first plurality of pulses that form a first burst of pulses; and wherein determining the second set of parameters of the second electrical signal comprises setting a second plurality of pulses that form a second burst of pulses to occur after delivering the first burst of pulses.

Clause 3. The method of clause 2, wherein the first burst of pulses comprises a first number of pulses that is different than a second number of pulses of the second burst of pulses.

Clause 4. The method of any combination of clauses 2-3, wherein the first burst of pulses comprises a first duration that is different than a second duration of the second burst of pulses.

Clause 5. The method of clause 2, wherein the first burst of pulses comprises a first number of pulses equal to a second number of pulses of the second burst of pulses.

Clause 6. The method of any combination of clauses 2 or 5, wherein the first burst of pulses comprises a first duration that equals a second duration of the second burst of pulses.

Clause 7. The method of any combination of clauses 2-6, wherein the first electrical signal comprises a third plurality of pulses that form a third burst of pulses.

Clause 8. The method of clause 7, wherein the first burst of pulses comprises a first number of pulses that is different than a third number of pulses of the third burst of pulses.

Clause 9. The method of any combination of clauses 7-8, wherein the first burst of pulses comprises a first duration that is not equal to a third duration of the third burst of pulses.

Clause 10. The method of clause 7, wherein the first burst of pulses comprises a first number of pulses equal to a third number of pulses of the third burst of pulses.

Clause 11. The method of any combination of clauses 7 or 10, wherein the first burst of pulses comprises a first duration that equals a third duration of the third burst of pulses.

Clause 12. The method of clause 1, wherein determining the first set of parameters of the first electrical signal comprises determining a first portion of a plurality of interleaved pulses; and wherein determining the second set of parameters of the second electrical signal comprises determining a second portion of the plurality of interleaved pulses.

Clause 13. The method of clause 12, wherein the first portion of the plurality of interleaved pulses comprises a first pulse and a third pulse; and wherein the second portion of the plurality of interleaved pulses comprises a second pulse and a fourth pulse, wherein determining the second set of parameters of the second electrical signal comprises setting the second pulse to occur after the first pulse and before the third pulse and setting the fourth pulse to occur after the third pulse.

Clause 14. The method of clause 12, wherein the plurality of interleaved pulses is a first plurality of interleaved pulses; wherein determining the first set of parameters of the first electrical signal comprises determining a first portion of a second plurality of interleaved pulses; and wherein determining the second set of parameters of the second electrical signal comprises determining a second portion of the second plurality of interleaved pulses.

Clause 15. The method of clause 14, wherein the first plurality of interleaved pulses comprises a first number of pulses that is not equal to a second number of pulses of the second plurality of interleaved pulses.

Clause 16. The method of clause 14, wherein the first plurality of interleaved pulses comprises a first number of pulses that is equal to a second number of pulses of the second plurality of interleaved pulses.

Clause 17. The method of clause 1, wherein the first electrical signal comprises a first portion of a plurality of concurrent pulses; and wherein determining the second set of parameters of the second electrical signal comprises setting a second portion of the plurality of concurrent pulses to be delivered concurrently with the delivery of the first portion of the plurality of concurrent pulses.

Clause 18. The method of clause 17, wherein the first portion of the plurality of concurrent pulses comprises a first pulse and a third pulse; and wherein the second portion of the plurality of concurrent pulses comprises a second pulse and a fourth pulse, wherein determining the second set of parameters of the second electrical signal comprises setting the second pulse to be delivered concurrently with the first pulse and setting the fourth pulse to be delivered concurrently with the third pulse.

Clause 19. The method of clause 17, wherein the plurality of concurrent pulses is a first plurality of concurrent pulses; wherein the first electrical signal comprises a first portion of a second plurality of concurrent pulses; and wherein determining the second set of parameters of the second electrical signal comprises setting a second portion of the second plurality of concurrent pulses to be delivered concurrently with the delivery of the first portion of the second plurality of concurrent pulses.

Clause 20. The method of any combination of clauses 1-19, further comprising: sensing, by the one or more processors, one or more patient parameters while pausing the first electrical signal and the second electrical signal; and wherein determining the first set of parameters of the first electrical signal, determining the second set of parameters of the second electrical signal, or determining both the first set of parameters of the first electrical signal and determining the second set of parameters of the second electrical signal is based on the one or more patient parameters.

Clause 21. The method of any combination of clauses 1-20, wherein the first region of the brain is in a first hemisphere of the brain; and wherein the second region of the brain is in a second hemisphere of the brain.

Clause 22. The method of any combination of clause 1-20, wherein the first region of the brain and the second region of the brain are arranged in different regions of a single hemisphere of the brain.

Clause 23. The method of any combination of clause 1-22, wherein the first electrical signal comprises a first plurality of pulses, each pulse of the first plurality of pulses comprising a continuous-time signal; and wherein the second electrical signal comprises a second plurality of pulses, each pulse of the second plurality of pulses comprising the continuous-time signal.

Clause 24. The method of clause 23, wherein the continuous-time signal comprises one or more of a sine wave at 130 Hz or a cosine wave at 130 Hz.

Clause 25. A medical device comprising processing circuitry configured to perform the method of any combination of clause 1-24.

Clause 26. The medical device of clause 25, wherein the medical device comprises an implantable medical device.

Clause 27. A system for providing stimulation to a patient comprising processing circuitry configured to perform the method of any of clauses 1-24.

Clause 28. A computer-readable storage medium having stored thereon instructions that, when executed, cause processing circuitry to perform the method of any of clause 1-24.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A medical device for providing electrical stimulation to a brain of a patient, the medical device comprising one or more processors configured to:
   determine a first timing associated with a first burst of pulses for a first electrical signal deliverable to a first region of the brain;
   determine a second timing, following the first timing, associated with a second burst of pulses for a second electrical signal deliverable to a second region of the brain using, as input,
      a determined strength of synchrony between the first region of the brain and the second region of the brain;
   deliver, at the first timing via a first electrode, the first electrical signal to the first region of the brain; and
   deliver, at the second timing via a second electrode, the second electrical signal to the second region of the brain.

2. The medical device of claim 1, wherein the first burst of pulses comprises a first number of pulses that is different than a second number of pulses of the second burst of pulses.

3. The medical device of claim 1, wherein the first burst of pulses comprises a first duration that is different than a second duration of the second burst of pulses.

4. The medical device of claim 1, wherein the first burst of pulses comprises a first number of pulses equal to a second number of pulses of the second burst of pulses.

5. The medical device of claim 1, wherein the first burst of pulses comprises a first duration that equals a second duration of the second burst of pulses.

6. The medical device of claim 1, wherein the first electrical signal comprises a third plurality of pulses that form a third burst of pulses.

7. The medical device of claim 6, wherein the first burst of pulses comprises a first number of pulses that is different than a third number of pulses of the third burst of pulses.

8. The medical device of claim 6, wherein the first burst of pulses comprises a first duration that is not equal to a third duration of the third burst of pulses.

9. The medical device of claim 6, wherein the first burst of pulses comprises a first number of pulses equal to a third number of pulses of the third burst of pulses.

10. The medical device of claim 6, wherein the first burst of pulses comprises a first duration that equals a third duration of the third burst of pulses.

11. The medical device of claim 1, wherein the first burst of pulses comprises a first portion of a plurality of burst interleaved pulses, wherein the second burst of pulses comprises a second portion of the plurality of burst interleaved pulses, and wherein the one or more processors are additionally configured to:
   determine parameters of the first portion of the plurality of burst interleaved pulses; and
   determine parameters of the second portion of the plurality of burst interleaved pulses.

12. The medical device of claim 11,
   wherein the first portion of the plurality of burst interleaved pulses comprises a first one or more pulses and a third one or more pulses; and
   wherein the second portion of the plurality of burst interleaved pulses comprises a second one or more pulses and a fourth one or more pulses, wherein the second one or more pulses occur after the first one or more pulses and before the third one or more pulses and the fourth one or more pulses occur after the third one or more pulses.

13. The medical device of claim 1, wherein the one or more processors are configured to:
   determine a first plurality of pulses that form the first burst of pulses; and
   a second plurality of pulses that form the second burst of pulses such that a first pulse of the second burst of pulses overlaps with at least one pulse of the first burst of pulses and a second pulse of the second burst of pulses does not overlap with any pulse of the first burst of pulses.

14. The medical device of claim 13,
   wherein the first burst of pulses comprises a first burst frequency; and
   wherein the second burst of pulses comprises a second burst frequency that is different than the first burst frequency.

15. The medical device of claim 1, wherein to determine the second timing using, as input, the determined strength of synchrony between the first region of the brain and the second region of the brain, the one or more processors are configured to:
   compare oscillatory activity between one or more neurons of the first region of the brain and one or more neurons of the second region of the brain to an oscillatory activity threshold;
   based on the comparison, determine the strength of synchrony between the first region of the brain and the second region of the brain; and
   using the determined strength of synchrony as input, determine the second timing, the second timing being associated with desynchronization of the first region of the brain and the second region of the brain.

16. A method for providing electrical stimulation to a brain of a patient, the method comprising:
   determining, with one or more processors, a first timing associated with a first burst of pulses for a first electrical signal deliverable to a first region of the brain via a first electrode;
   determining, with the one or more processors, a second timing, following the first timing, associated with a second burst of pulses for a second electrical signal deliverable to a second region of the brain via a second electrode using, as input,
      a determined strength of synchrony between the first region of the brain and the second region of the brain;

delivering, with the one or more processors and at the first timing with the first electrode, the first electrical signal to the first region of the brain; and delivering, with the one or more processors and at the second timing with the second electrode, the second electrical signal to the second region of the brain.

17. A medical device comprising:

a first electrode;

a second electrode; and processing circuitry configured to:
- determine a first timing associated with a first burst of pulses for a first electrical signal deliverable to a first region of a brain of a patient;
- determine a second timing, following the first timing, associated with a second burst of pulses for a second electrical signal, deliverable to a second region of the brain using, as input,
- a determined strength of synchrony between the first region of the brain and the second region of the brain;

deliver, at the first timing and with the first electrode, the first electrical signal to the first region of the brain; and deliver, at the second timing and with the second electrode, the second electrical signal to the second region of the brain.

* * * * *